(12) United States Patent
Jang et al.

(10) Patent No.: US 11,884,931 B2
(45) Date of Patent: Jan. 30, 2024

(54) ONCOLYTIC VIRUS FOR COLORECTAL CANCER TREATMENT USING COLORECTAL CANCER CELL-SPECIFIC INFECTIOUS NEWCASTLE DISEASE VIRUS AND COMPOSITION FOR COLORECTAL CANCER TREATMENT USING SAME

(71) Applicant: LIBENTECH CO., LTD., Daejeon (KR)

(72) Inventors: Hyun Jang, Danwon-gu (KR); Bo Kyoung Jung, Busan (KR); Yong Hee An, Sejong-si (KR)

(73) Assignee: LIBENTECH CO., LTD., Daejeon (KR)

( * ) Notice: Subject to any disclaimer, the term of this patent is extended or adjusted under 35 U.S.C. 154(b) by 218 days.

(21) Appl. No.: 17/606,931

(22) PCT Filed: Sep. 27, 2021

(86) PCT No.: PCT/KR2021/013148
§ 371 (c)(1),
(2) Date: Oct. 27, 2021

(87) PCT Pub. No.: WO2023/013812
PCT Pub. Date: Feb. 9, 2023

(65) Prior Publication Data
US 2023/0121063 A1 Apr. 20, 2023

(30) Foreign Application Priority Data
Aug. 6, 2021 (KR) .......................... 10-2021-0103937

(51) Int. Cl.
*C12N 15/86* (2006.01)
*A61K 35/768* (2015.01)
*A61P 1/00* (2006.01)
*A61P 35/00* (2006.01)
*G01N 33/569* (2006.01)

(52) U.S. Cl.
CPC ............ *C12N 15/86* (2013.01); *A61K 35/768* (2013.01); *A61P 1/00* (2018.01); *A61P 35/00* (2018.01); *G01N 33/56983* (2013.01); *C12N 2760/18121* (2013.01); *C12N 2760/18132* (2013.01); *C12N 2760/18143* (2013.01); *C12N 2760/18152* (2013.01); *C12N 2760/18171* (2013.01)

(58) Field of Classification Search
None
See application file for complete search history.

(56) References Cited

U.S. PATENT DOCUMENTS

2014/0271677 A1 9/2014 Palese et al.

FOREIGN PATENT DOCUMENTS

| KR | 10-2008-0028277 A | 3/2008 |
| KR | 10-2015-0127164 A | 11/2015 |
| KR | 10-2020-0004408 A | 1/2020 |
| WO | 2018/209194 A2 | 11/2018 |
| WO | 2019/197275 A1 | 10/2019 |

OTHER PUBLICATIONS

Office Action dated Apr. 25, 2022 in Korean Application No. 10-2021-0103937.
Office Action dated Jul. 4, 2022 in Korean Application No. 10-2021-0103937.
Tirumurugaan et al., "Genotypic and Pathotypic Characterization of Newcastle Disease Viruses from India", PloS ONE, Dec. 2011, vol. 6, Issue 12, e28414, pp. 1-10 (10 pages total).
Rangaswamy et al., "Newcastle Disease Virus Establishes Persistent Infection in Tumor Cells In Vitro: Contribution of the Cleavage Site of Fusion Protein and Second Sialic Acid Binding Site of Hemagglutinin-Neuraminidase", Journal of Virology, Aug. 2017, vol. 91, Issue 16, e00770-17, pp. 1-17 (17 pages total).
Written Decision on Registration dated Nov. 28, 2022 in Korean Application No. 10-2021-0103937.

*Primary Examiner* — Robert M Kelly
(74) *Attorney, Agent, or Firm* — Sughrue Mion, PLLC

(57) ABSTRACT

Provided is an M2-LVP-K1 virus including a colorectal cancer cell-specific mutant sialic acid binding domain and a composition for treating colorectal cancer including the same. The mutant sialic acid binding domain is constructed using directed evolution technology, and is a recombinant Newcastle disease virus constructed by substituting a normal sialic acid binding domain for a HN protein, a cell-binding receptor, to improve the specific infectivity to HCT116 cells. It was identified that M2-LVP-K1 recombinant Newcastle disease virus with improved colorectal cancer cell-specific infectivity has improved HCT116 cell death effect compared to the conventional normal recombinant Newcastle disease virus, and produces an excellent effect in inhibiting cancer tissue growth through in vivo experiments. The mutant recombinant Newcastle disease virus presented in this study relates to a therapeutic viral agent capable of inducing clinical symptom reduction, partial remission, or complete remission through colorectal cancer cell death or colorectal cancer tissue shrinkage.

6 Claims, 18 Drawing Sheets

Specification includes a Sequence Listing.

FIG. 2

| OD450nm | 1 | 2 | 3 | 4 | 5 | 6 | 7 | 8 | 9 | 10 | 11 | 12 |
|---|---|---|---|---|---|---|---|---|---|---|---|---|
| A | 0.149 | 0.116 | 0.109 | 0.109 | 0.107 | 0.095 | 0.096 | 0.124 | 0.112 | 0.117 | 0.113 | 0.106 |
| B | 0.123 | 0.117 | 0.108 | 0.098 | 0.099 | 0.11 | 0.099 | 0.114 | 0.108 | 0.115 | 0.12 | 0.101 |
| C | 0.129 | 0.123 | 0.977 | 0.103 | 0.1 | 0.104 | 0.124 | 0.338 | 0.1 | 0.105 | 0.108 | 0.117 |
| D | 0.112 | 0.153 | 0.136 | 0.094 | 0.096 | 0.096 | 0.1 | 0.114 | 0.098 | 0.12 | 0.1 | 0.103 |
| E | 0.118 | 0.117 | 0.115 | 0.098 | 0.109 | 0.104 | 0.099 | 0.094 | 0.102 | 0.102 | 0.302 | 0.1 |
| F | 0.122 | 0.107 | 0.119 | 0.107 | 0.342 | 0.109 | 0.115 | 0.111 | 0.117 | 0.118 | 0.107 | 0.102 |
| G | 0.11 | 0.124 | 0.136 | 0.13 | 0.107 | 0.196 | 0.107 | 0.102 | 0.105 | 0.105 | 0.11 | 0.096 |
| H | 0.138 | 0.097 | 0.096 | 0.086 | 0.101 | 0.11 | 0.098 | 0.08 | 0.105 | 0.088 | 0.127 | 0.086 |

| Virus | Virus adaptation cell | Titration cell ($10^A$ TCID$_{50}$/mL) | |
|---|---|---|---|
| | | Vero76 | HCT116 |
| LVP-K1 | Vero76 | 4.7 | 3.7 |
| M2-LVP-K1 | Vero 76 | 3.7 | 4.1 |
| M2-LVP-K1 | HCT116 | 4.9 | 5.5 |

*Vero76 cells were infected with LVP-K1 or M2-LVP-K1 virus at an MOI of 0.1. HCT116 cells were infected with M2-LVP-K1 virus at an MOI of 0.1. At 48 hours post infection, virus titers were determined using TCID$_{50}$ titrations on different cells (Vero76 and HCT116 cells).

ONCOLYTIC VIRUS FOR COLORECTAL CANCER TREATMENT USING COLORECTAL CANCER CELL-SPECIFIC INFECTIOUS NEWCASTLE DISEASE VIRUS AND COMPOSITION FOR COLORECTAL CANCER TREATMENT USING SAME

CROSS-REFERENCE TO RELATED APPLICATIONS

This application is a National Stage of International Application No. PCT/KR2021/013148 filed Sep. 27, 2021, which claims priority to Korean Patent Application No. 10-2021-0103937 filed Aug. 6, 2021, the entire disclosures of which are incorporated herein by reference.

TECHNICAL FIELD

The present disclosure relates to a development of an oncolytic virus for treating colorectal cancer, and a treatment and a therapeutic agent using the same, and more particularly, to an oncolytic virus for treating colorectal cancer using a colorectal cancer cell-specific infectious Newcastle disease virus and a composition for treating colorectal cancer using the same.

BACKGROUND ART

Colorectal cancer is the third most frequently occurring disease among all cancers, and is the disease with the highest mortality rate among all cancers worldwide. The incidence is rapidly increasing in Asia, including Korea, and according to 2016 Korean statistics, it has the third highest mortality rate. If colorectal cancer is detected at an early stage, the lifespan of more than 90% of subjects increases by 5 years or more, but only 40% of patients are diagnosed with colorectal cancer at an early stage. Early diagnosis of colorectal cancer is directly related to a patient's life, and remains a challenging task to date.

The rectum is the last part of the large intestine and is a pipe-shaped tube with a length of about 15 cm, and is divided from the inside into the mucosal layer, the submucosal layer, the muscular layer, and the serosal layer. Most rectal cancers are adenocarcinomas occurring in the intestinal mucosa. In addition, it is known that there are carcinoid tumors, lymphomas, sarcomas, squamous cell carcinomas, and metastatic cancers. Cancer that occurs in the colon is called colon cancer. It is also histologically most of the adenocarcinoma originating from the mucosa. Rarely, cancer is caused by neuroendocrine tumors, lymphomas, and the like. In general, colon cancer also refers to adenocarcinoma. Since most colorectal cancers have the form of polyps before they develop into adenocarcinoma, early diagnosis to detect the presence of these polyps through colonoscopy is very important. However, not all polyps develop into cancer, and the potential of malignancy is classified according to histological characteristics.

Oncolytic virus treatment is taking a new approach as a new biopharmaceutical for cancer treatment, and has made significant advances at the experimental and clinical levels. Recently, the oncolytic virus used for virus treatment uses a method of using the virus itself having oncolytic properties, a method of using a virus inserted with a gene that acts specifically for cancer cells and has an effect on killing cancer cells, or both methods.

However, the oncolytic virus cannot specifically infect specific cancer cells and cannot kill only the cancer cells. When the oncolytic virus for various cancers is injected intravenously, there is a drawback in that the concentration of the virus that infects cancer cells and acts is reduced by the dilution effect primarily caused by blood. In order to prepare for the reduction in efficacy due to the dilution effect, a very high concentration of the oncolytic virus is being used, thereby producing the effects of inducing an immune response causing secondary side effects, and reducing efficacy.

Recombinant Newcastle disease virus (NDV) used in the present disclosure is also a representative intrinsic oncolytic virus, which infects cancer cells without specific gene insertion and has various mechanisms for inducing apoptosis of cancer cells and inducing immune responses to cancer cells. Infection of cancer cells induces cancer cell death, but normal cells are also infected, and virus replication and proliferation cannot occur in normal cells due to the NDV removal function by Interferon-α. Accordingly, recombinant NDV is also an oncolytic virus without cancer cell-specific infectivity.

In NDV, cell infection is initiated by the binding of HN protein to sialic acid on the cell surface. HN protein binds to a sialic acid (glycoprotein) on the cell surface, and then cleaves the bound sialic acid by neuramidase and causes fusion of the cell membrane of host cells and the envelope of NDV virus by F protein, so that the RNA genome of the NDV virus enters the cytoplasm to infect the cell. The sialic acid binding of the HN protein binds to the sialic acid on the cell surface through four sialic acid binding motifs present in the globular head domain. Each motif is divided into HN protein-amino acid sequences 156 to 174, 171 to 203, 515 to 527, and 547 to 556, and four motifs spatially bind to sialic acid while anchored in the virus envelope. The types of cells that may be infected with the NDV virus are relatively diverse, and it may be assumed that the sialic acid binding of the HN protein is not very specific. The essential technology for developing a therapeutic agent for NDV oncolytic virus is first to construct a virus having cancer cell-specific infectivity, and second, to insert a gene that induces cancer cell death in the most optimal location.

Accordingly, in the present disclosure, an attempt was made to develop a virus capable of cancer cell-specific infection by making a mutation in the globular head domain (hereafter referred to as H domain), which is the sialic acid binding site of the HN protein using directed evolution technology, and constructing a recombinant NDV with specificity for colorectal cancer-specific cells among these mutations. In other words, it is to produce an oncolytic virus based on H domain mutant NDV vector and develop a virus preparation for colorectal cancer treatment through efficacy evaluation using the same.

DISCLOSURE

Technical Problem

The present disclosure has been made in an effort to provide a recombinant vector for constructing a colorectal cancer-targeted oncolytic virus including a Newcastle disease virus (NDV) cDNA containing a gene encoding NP, P, M, F, HN and L proteins and a gene encoding a mutation H domain (globular head domain) represented by any one of nucleotide sequences represented by SEQ ID NOS: 3 to 7.

In addition, the present disclosure has been also made in an effort to provide an oncolytic virus for treating colorectal cancer including the recombinant vector for constructing the oncolytic virus.

In addition, the present disclosure has been also made in an effort to provide a pharmaceutical composition for preventing or treating colorectal cancer including the oncolytic virus for treating colorectal cancer as an active ingredient.

In addition, the present disclosure has been also made in an effort to provide a method for selecting an H domain that specifically infects a target cancer cell.

In addition, the present disclosure has been also made in an effort to provide a method for preventing or treating colorectal cancer.

In addition, the present disclosure has been also made in an effort to provide a method for providing information for preventing or treating colorectal cancer.

In addition, the present disclosure has been also made in an effort to provide a method for evaluating an effect of preventing or treating colorectal cancer in animals.

In addition, the present disclosure has been also made in an effort to provide a method for producing a recombinant Newcastle disease virus.

Technical Solution

An exemplary embodiment of the present disclosure provides a recombinant vector for constructing a colorectal cancer-targeted oncolytic virus including a Newcastle disease virus (NDV) cDNA containing genes encoding NP, P, M, F, HN and L proteins and a gene encoding a mutation H domain (globular head domain) represented by any one of nucleotide sequences represented by SEQ ID NOS: 3 to 7.

Another exemplary embodiment of the present disclosure provides an oncolytic virus for treating colorectal cancer including the recombinant vector for constructing the oncolytic virus.

Yet another exemplary embodiment of the present disclosure provides a pharmaceutical composition for preventing or treating colorectal cancer including the oncolytic virus for treating colorectal cancer as an active ingredient.

In addition, yet another exemplary embodiment of the present disclosure provides a method for selecting an H domain that specifically infects a target cancer cell, in which the method includes: producing a mutation H domain by randomly generating a mutation in a gene encoding the H domain of an HN protein of a Newcastle disease virus represented by a nucleotide sequence represented by SEQ ID NO: 8; fusing an avidin protein and the mutation H domain to produce a mutation H domain-avidin fusion protein; treating a target cancer cell with the H domain-avidin fusion protein; and measuring an expression level of the mutation H domain-avidin fusion protein.

In addition, yet another exemplary embodiment of the present disclosure provides a method for preventing or treating colorectal cancer, in which the method includes administering the composition to a subject excluding a human.

In addition, yet another exemplary embodiment of the present disclosure provides a method for providing information for preventing or treating colorectal cancer, in which the method includes: administering the pharmaceutical composition to a subject; and measuring and evaluating changes in cancer cells or cancer tissues of a subject.

In addition, yet another exemplary embodiment of the present disclosure provides a method for evaluating an effect of preventing or treating colorectal cancer in animals, in which the method includes administering the pharmaceutical composition to an animal excluding a human.

In addition, yet another exemplary embodiment of the present disclosure provides a method for producing a recombinant Newcastle disease virus, in which the method includes: inoculating the recombinant Newcastle disease virus into a host cell line; culturing the host cell line; and obtaining the recombinant Newcastle disease virus from a culture of the host cell line.

Advantageous Effects

According to the exemplary embodiments of the present disclosure, the present disclosure uses a Newcastle disease virus (NDV) to artificially mutate the sialic acid-binding globular domain gene of the HN protein, which serves as a receptor for host cell infection, to increase colorectal cancer cell binding ability and increase colorectal cancer cell killing effect. Thus, a transgene cassette capable of introducing a gene inducing cancer apoptosis is inserted between the structural genes, making it possible to insert a foreign gene that can increase the efficacy of cancer treatment. Accordingly, by developing a colorectal cancer cell-specific oncolytic virus, a safe and effective colorectal cancer therapeutic agent was developed, which may contribute to the treatment of colorectal cancer by treating patients with colorectal cancer and inhibiting the aggravation of colorectal cancer.

DESCRIPTION OF DRAWINGS

Figure 2:
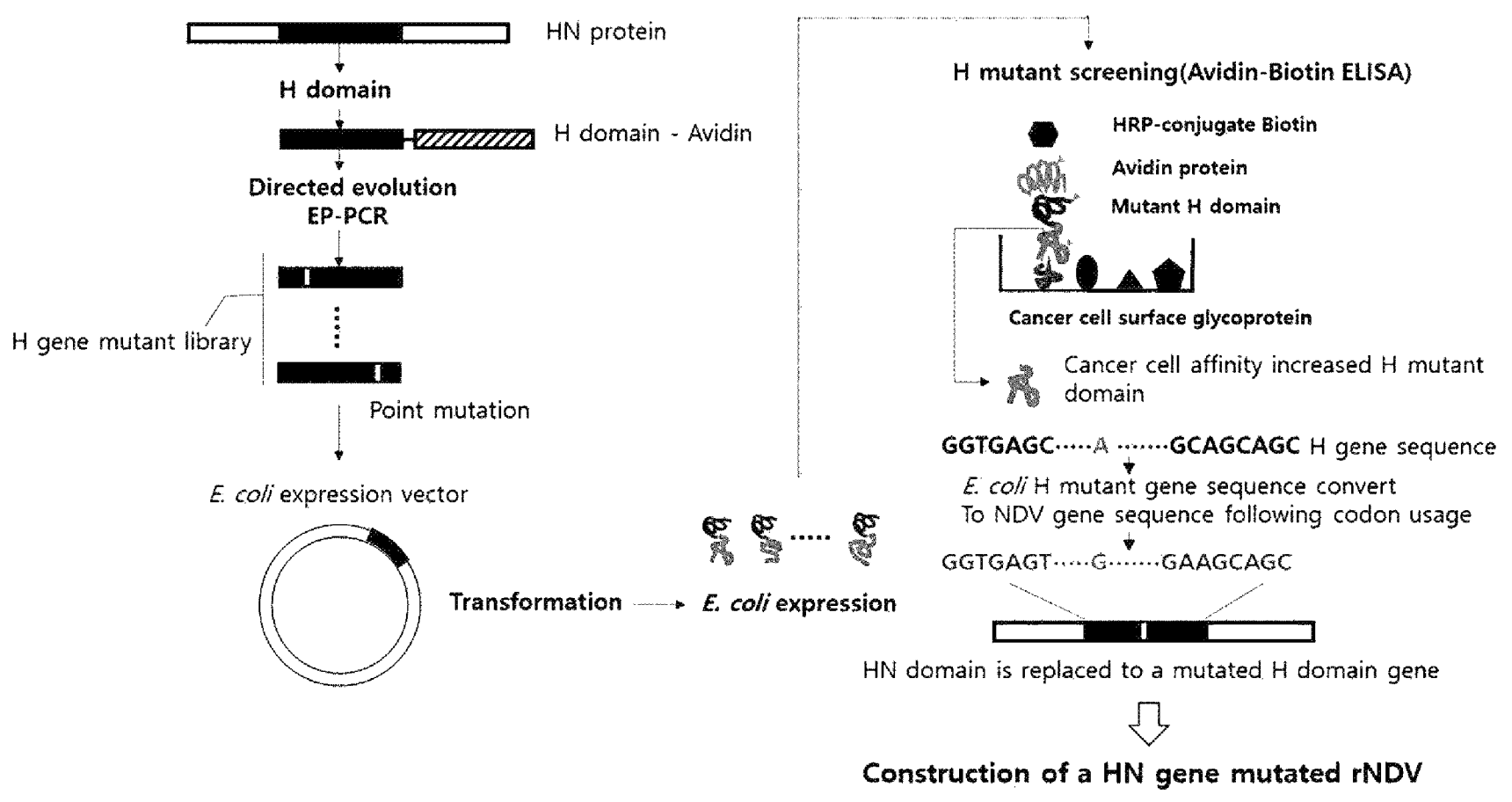

FIG. 2 is a diagram schematically showing the application of directed evolution technology for the construction of an H domain protein with improved binding ability to cancer cells.

FIGS. 6A-6C are schematic diagrams of a gene of a vector for constructing a colorectal cancer-targeted oncolytic virus, a schematic diagram for constructing a recombinant Newcastle disease virus, and a diagram showing the RT-PCR product for identification of removal of the Vaccinia virus.

FIG. 7 is a diagram showing experimental results comparing the proliferative capacity of the M2-LVP-K1 virus recovered after transfection in HCT116 cells and Vero76 cells.

MODES OF THE INVENTION

Figure 1:
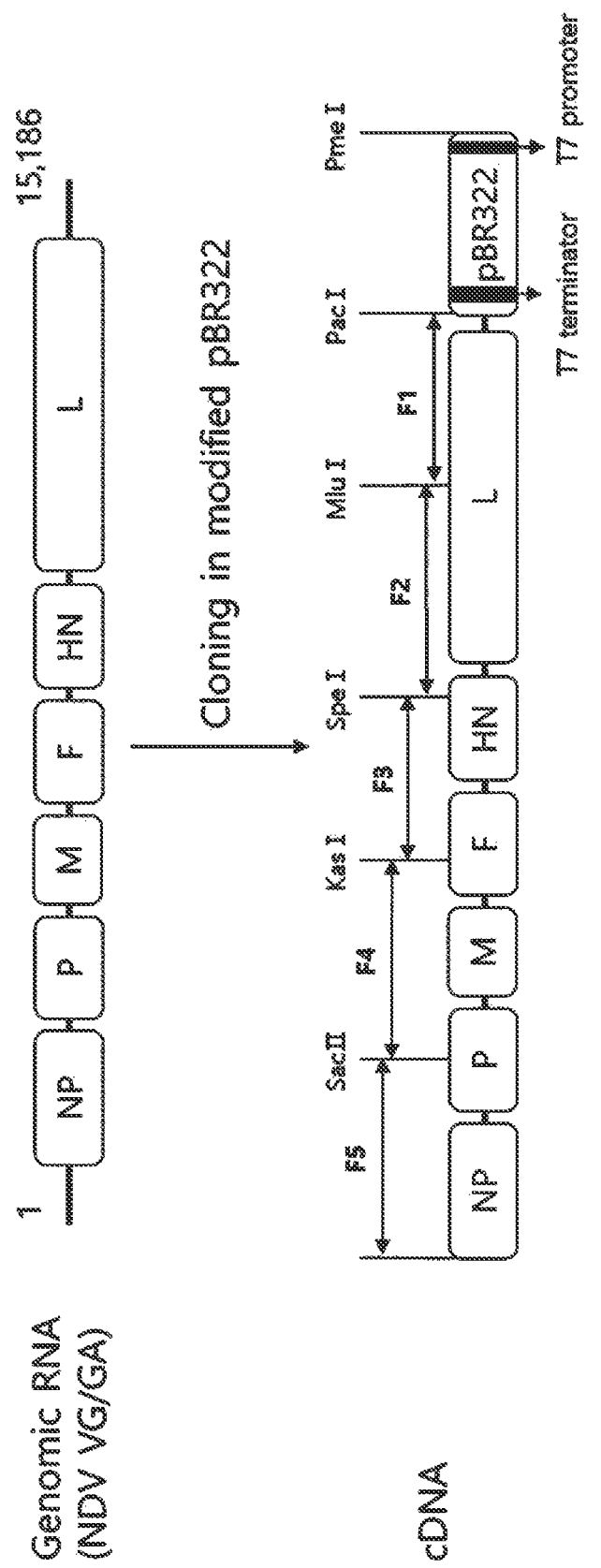
FIG. 1 is a diagram showing an insertion process into a modified pBR322 vector by synthesizing a NDV VG/GA strain of the present disclosure with cDNA.

Hereinafter, the present disclosure will be described in detail by way of Examples of the present disclosure with reference to the accompanying drawings. However, the following Examples are provided by way of illustration of the present disclosure. When it is determined that the specific description of known techniques or configuration well known to those skilled in the art unnecessarily obscure the gist of the present disclosure, the detailed description therefor may be omitted, and the present disclosure is not limited thereto. The present disclosure allows various modifications and applications within the description of the claims to be described later and the scope of equivalents interpreted therefrom.

Further, terminologies used herein are terms used to properly represent preferred Examples of the present disclosure. It may vary depending on the intent of users or operators, or custom in the art to which the present disclosure belongs. Accordingly, the definitions of these terms should be based on the contents throughout this specification. In the entire specification, when a part is referred to as "comprising" a component, it means that it may further include other components without excluding other components unless specifically described otherwise.

Throughout the specification, "%" used to refer to the concentration of specific substance is (weight/weight) % for solid/solid, (weight/volume) % for solid/liquid and (volume/volume) % for liquid/liquid, unless specified otherwise.

Hereinafter, the present disclosure will be described in more detail.

An embodiment of the present disclosure provides a recombinant vector for constructing a colorectal cancer-targeted oncolytic virus including a Newcastle disease virus (NDV) cDNA containing genes encoding NP, P, M, F, HN and L proteins and a mutation H domain (globular head domain).

In addition, the recombinant vector may further include a transgene cassette for foreign gene expression consisting of an IGS sequence (gene end (GE), intergenic sequence (IG), and gene start (GS)) and a multiple cloning site (MCS).

In addition, the foreign gene may be used without limitation as long as it is a foreign gene known to induce colorectal cancer apoptosis which may enhance the colorectal cancer cell death effect.

In addition, the transgene cassette is composed of a GE-IG-GS sequence and a multi cloning site (MCS) in front of the N-terminus of the foreign gene insertion site, and may be constructed by inserting the transgene cassette between the NP and P genes, between the P and M genes, and between the HN and L genes in compliance with the rule of six together with various restriction enzyme sequences. Preferably, the transgene cassette may be inserted between the NP and P genes, and between the P and M genes, and more preferably, the transgene cassette may be inserted between the NP and P genes.

In the Newcastle disease virus, an IGS (GE-IG-GS) sequence exists between each gene, and each gene undergoes a transcriptional process in the initial stage of host cell infection to synthesize a movement protein to the endoplasmic reticulum (ER) of the host cell. Then, when the amount of M protein synthesis rises above a certain level, a (+)sense RNA genome is synthesized and a (−)sense RNA genome is synthesized using this as a template. The finished virus particles are released out of the cell.

It is known that the ability of the Newcastle disease virus to introduce foreign genes is up to 6 kb, and the introduction of foreign genes has been mainly made between the P and M genes and between the HN and L genes. However, although it is known that the foreign genes may be introduced between all of the six genes, it is known that each location has an effect on mRNA expression, protein expression, and, in severe cases, virus proliferation. However, quantitative comparison tests for each location have not been performed. There is a GE-IG-GS gene between each gene. In particular, in the case of an IG gene, it is made up of 1 or 2 nucleotides between NP-P, P-M and M-F, 35 nucleotides between F-HN, and 47 nucleotides between HN-L. After virus infection, the (−)sense RNA genome synthesizes the mRNA of each protein at the initial stage of infection by the NP, P, and L proteins possessed by NDV, and the synthesized mRNA moves to the endoplasmic reticulum of the host cell to synthesize the protein of each gene. Thereafter, the (+)sense RNA genome is synthesized by the interaction of the NP, P, and L proteins with the M protein, and many copies of the (−)sense RNA genome are synthesized using this as a template and released out of the host cell. It is known that for the amount of mRNA synthesis for autologous protein production at the time of initial infection, N-terminus, in other words, NP mRNA is synthesized the most, and the mRNA synthesis decreases as it moves away from the N-terminus afterwards.

For cDNA construction of a Newcastle disease virus, a method of making the NDV (−)sense RNA genome into multiple fragments of double-stranded DNA through the reverse transcription polymerase chain reaction (RT-PCR) method, and then religating each fragment to create a cDNA clone of the entire NDV is being used. In cDNA preparation using this method, point mutation is highly likely to occur due to the nature of reverse transcriptase, so after the cDNA is finished preparing, the gene sequence of 15 kb is identified through sequencing. When one or more point mutation occur, a process of making cDNA from the NDV genome needs to be repeated again. Recombinant NDV is constructed by inserting the cDNA fragment into the pBR322 vector.

According to one embodiment of the present disclosure, the vector for constructing the colorectal cancer-targeted oncolytic virus may be constructed through an overlap cloning method after putting the transgene cassette for foreign gene expression in a perfectly made recombinant NDV between each gene, divide it into 4 fragments of DNA, ligating each NDV fragmented gene to pBR322 plasmid DNA, and then performing transformation into TOP10 *E. coli* to construct and store 4 types of recombinant strains, and then separating the gene from each recombinant *E. coli* strain when introducing a new gene and obtain a fragment of the gene using PCR, but is not limited thereto.

In addition, the vector constructed by the above method prevents point mutation that occurs during the process of making a recombinant Newcastle disease virus each time, and has a feature that a foreign gene may be easily inserted into the NDV cDNA through a multiple cloning site (MCS).

In addition, the recombinant vector of the present disclosure includes a mutant gene that enhances colorectal cancer cell-specific infection ability. The mutant gene may be a Newcastle disease virus hemagglutinin-neuraminidase (HN) gene, preferably an H domain gene of the HN protein. The mutation may be a mutation occurred in the amino acid sequences represented by SEQ ID NOS: 123 to 616 corresponding to the hemagglutinin protein-amino acid sequence of the HN protein, and more preferably, a mutation occurred in the amino acid sequences represented by SEQ ID NOS: 123 to 571 corresponding to the H domain gene.

As used herein, the term "H domain" refers to a sialic acid binding site of the HN protein of a Newcastle disease virus, and refers to a globular head domain with a length of about 51 kDa. HN protein binds to a sialic acid (glycoprotein) on the cell surface, and then cleaves the bound sialic acid by neuramidase and causes fusion of the cell membrane of host cells and the envelope of NDV virus by F protein, so that the RNA genome of the NDV virus enters the cytoplasm to infect the cell.

In addition, the mutation H domain may be represented by any one of nucleotide sequences represented by SEQ ID NOS: 3 to 7.

In addition, the mutation H domain protein encoded by a nucleotide sequence represented by SEQ ID NO: 3 may be one in which a 519th amino acid is substituted from serine to glycine.

In addition, the mutation H domain protein encoded by a nucleotide sequence represented by SEQ ID NO: 4 may be one in which a 267th amino acid is substituted from proline to glycine.

In addition, the mutation H domain protein encoded by a nucleotide sequence represented by SEQ ID NO: 5 may be one in which a 182nd amino acid is substituted from alanine to an aspartic acid.

In addition, the mutation H domain protein encoded by a nucleotide sequence represented by SEQ ID NO: 6 may be one in which a 418th amino acid is substituted from serine to proline.

In addition, in the mutation H domain protein encoded by a nucleotide sequence represented by SEQ ID NO: 7, a 319th amino acid may be substituted from glycine (serine) to alanine, a 325th amino acid may be substituted from proline to arginine, and a 392nd amino acid may be substituted from proline to histidine.

In addition, the vector for constructing the colorectal cancer-targeted oncolytic virus may be an M2-LVP-K1 vector composed of the nucleotide sequence represented by SEQ ID NO: 1, and includes a functionally equivalent substance thereto. The term "functionally equivalent substance" refers to a gene or gene combination including a sequence having at least 70%, preferably at least 80%, and more preferably at least 90% of homology with a gene sequence represented by SEQ ID NO: 1 as a result of a substitution or deletion of a nucleotide, and exhibiting substantially identical physiological activity to the gene having the gene sequence represented by SEQ ID NO: 1.

An embodiment of the present disclosure provides an oncolytic virus for treating colorectal cancer including the recombinant vector for constructing the oncolytic virus.

Since the oncolytic virus of the present disclosure includes the above-described recombinant vector for constructing the oncolytic virus, the description of the contents overlapping with the above-described recombinant vector for constructing the oncolytic virus of the present disclosure is omitted in order to avoid the excessive complexity of the present specification due to the overlapping description.

Examples of viruses that may be used for the vector for constructing the colorectal cancer-targeted oncolytic virus of the present disclosure include a lentivirus, a retrovirus, a vaccinia virus, an adenovirus, and an adeno-associated virus, a cytomegalovirus, a Sendai virus, a poxvirus, a Newcastle disease virus, and an alphavirus, but is not limited thereto. Any virus capable of expressing a protein through introduction of a foreign gene and capable of producing high stability, high expression ability and high viral titer may be used without limitation. Preferably, it may be an enveloped virus such as a vaccinia virus, a poxvirus, a flavivirus, an alphavirus, and a Newcastle disease virus, which not only transfer genes but also facilitate protein expression on the surface of the virus. More preferably, it may be a Newcastle disease virus (NDV) that is a safe virus without human infectivity and capable of producing a high viral titer, and still more preferably, a recombinant Newcastle disease virus (Accession No. KCTC14630BP).

As used herein, the term "Newcastle disease virus (NDV)" belongs to a paramyxovirus having a (−)sense RNA genome of about 15 kb and is known as a safe virus for mammals without human infectivity. NDV genomic RNA has an extragenic leader sequence of about 30 bases and a tail sequence of about 50 bases. Two sequences at both termini are known to control the transcription and replication of viral genes and the encapsidation of newly synthesized RNA genomes into viral particles. The NDV gene configuration consists of six genes including NP, P, M, F, HN and L between both terminal leaders and tail genes, and each gene encodes a nucleoprotein (NP), a phosphoprotein (P), a matrix protein (M), a fusion protein (F), a hemagglutinin-neuraminidase protein (HN), and a large protein (L).

The Newcastle disease virus is a legal infectious disease that infects chickens and causes neurological and respiratory symptoms, and is a very lethal virus for chickens. According to the pathogenicity, it is divided into velogenic, mesogenic, and lentogenic Newcastle disease viruses, all of which may be used in the production of foreign gene transfer virus vectors, but preferably mesogenic and lentogenic viruses may be used. More preferably, it may be a recombinant virus using a lentogenic virus strains.

As the Newcastle disease virus that may be used in the present disclosure, various strains such as Clone30, B1, 73T, Lasota, HJU, MTH-68, Ulster, and VG/GA may be used. Without being limited thereto, a newly isolated Newcastle disease virus may also be used, preferably Lasota, HJU, MTN-68, Ulster, and VG/GA strain, and more preferably Ulster and VG/GA strain, which are mesogenic or lentogenic viruses. Most preferably, VG/GA strain may be used, but is not limited thereto.

In addition, the recombinant Newcastle disease virus (Accession No. KCTC14630BP) may be one into which the M2-LVP-K1 vector represented by the nucleotide sequence represented by SEQ ID NO: 1 is introduced, and includes a functionally equivalent substance. The term "functionally equivalent substance" refers to a gene or gene combination including a sequence having at least 70%, preferably at least 80%, and more preferably at least 90% of homology with a gene sequence represented by SEQ ID NO: 1 as a result of a substitution or deletion of a nucleotide, and exhibiting substantially identical physiological activity to the gene having the gene sequence represented by SEQ ID NO: 2.

In addition, the oncolytic virus for treating colorectal cancer may include a mutation H domain to specifically infect colorectal cancer cells.

An embodiment of the present disclosure provides a pharmaceutical composition for preventing or treating colorectal cancer including the oncolytic virus for treating colorectal cancer as an active ingredient.

Since the pharmaceutical composition of the present disclosure includes the above-described recombinant vector for constructing the oncolytic virus, the description of the contents overlapping with the above-described recombinant vector for constructing the oncolytic virus of the present disclosure is omitted in order to avoid the excessive complexity of the present specification due to the overlapping description.

As used herein, the term "cancer" indicates a state that the abnormal cells which should be normally killed but alive and excessively proliferated by control disorder of cell itself, invade surrounding tissues and organs, to form lumps and destroy or modify the existing structure, and the cancer is used interchangeably with the malignancy.

As used herein, the term "prevention" refers to all actions that inhibit or delay progress of cancer by administering a composition of the present disclosure.

As used herein, the term "treatment" refers to all actions that alleviate or beneficially change cancer by administering a composition of the present disclosure, and refers to an approach for obtaining beneficial or desired results, including clinical results. Beneficial or desired clinical results include, but are not limited to, alleviation or amelioration of one or more symptoms or conditions, diminishment of the extent of disease, stabilization of the state of disease, prevention of development of disease, prevention of the spread of disease, delay or slowing of disease progression, delay or slowing of disease onset, amelioration or palliation of the disease state, and remission (whether partial or total). Those of ordinary skill in the technical field to which the present disclosure belongs will identify the exact criteria of a disease in which the composition of the present disclosure is effective and determine the degree of alleviation, improvement and treatment with reference to the data presented by the Korean Medical Association.

The virus of the present disclosure may be administered alone or in combination with other therapies, including chemotherapy, radiation therapy or other anti-viral therapies. For example, the virus may be administered either prior to or following surgical removal of a primary tumor or prior to, concurrently with, or following treatment such as administration of radiotherapy or conventional chemotherapeutic drugs. The virus may be administered in combination with, or in a sequential fashion with, other oncolytic viruses, which may demonstrate specificity for varying tumor cell types. Examples of the therapies conventionally used to treat, prevent or manage cancer include, but are not limited to, surgery, chemotherapy, radiation therapy, hormonal therapy, biological therapy and immunotherapy.

The pharmaceutical composition of the present disclosure is administered in a pharmaceutically effective amount. As used herein, the term "pharmaceutically effective amount" refers to an amount sufficient for the treatment of diseases at a reasonable benefit/risk ratio applicable to a medical treatment without causing any adverse effects, and the level of the effective dose may be determined based on the factors including the health conditions of a patient, type of disease (s), severity of illness, drug activity, sensitivity to drug, administration method, administration time, administration route and excretion rate, duration of treatment, factors including drug(s) to be mixed or concurrently used in combination, and other factors well known in the medical field. The composition of the present disclosure may be administered as an individual therapeutic agent, in combination with other therapeutic agents, or sequentially or simultaneously with conventional therapeutic agents, and may be administered once or multiple times. It is important to administer the composition in an amount to obtain the maximum effect with a minimum amount without adverse effects considering all of the factors described above, which may be easily determined by those skilled in the art.

As used herein, the term "subject" is not particularly limited as long as it is a subject for the purpose of preventing or treating colorectal cancer, and an animal including a human, for example, a mammal including a non-primate (for example, a cow, pig, horse, cat, dog, rat, and mouse) and a primate (for example, monkeys such as cynomolgus monkeys and chimpanzees). In some cases, it may be a subject excluding a human.

In addition, the composition of the present disclosure may be administered orally or parenterally during clinical administration, and may be used in the form of a general pharmaceutical formulation. Examples of dosage forms include, but are not limited to: oral, mucosal (for example, nasal, sublingual, vaginal, buccal, or rectal), parenteral (for example, subcutaneous, intravenous, bolus injection, intramuscular, or intraarterial), topical (for example, eyes), transdermal or transcutaneous administration. Examples of dosage forms include, but are not limited to: tablets; caplets; capsules, such as soft elastic gelatin capsules; cachets; troches; lozenges; dispersions; suppositories; powders; aerosols (for example, nasal sprays or inhalers); gels; liquid dosage forms suitable for oral or mucosal administration to a patient, including suspensions (for example, aqueous or non-aqueous liquid suspensions, oil-in-water emulsions, or water-in-oil liquid emulsions), solutions, and elixirs; liquid dosage forms suitable for injection administration to a patient; eye drops or other ophthalmic preparations suitable for topical administration; and sterile solids (for example, crystalline or amorphous solids) that can be reconstituted to provide liquid dosage forms suitable for injection administration to a patient. The composition, shape, and type of dosage forms of the present disclosure will typically vary depending on their use. For example, a dosage form used in the acute treatment of a disease may contain larger amounts of the active ingredients than a dosage form used in the chronic treatment of the same disease. Similarly, a parenteral dosage form may contain smaller amounts of the active ingredients than an oral dosage form used to treat the same disease. The dosage forms and ways compassed by the present disclosure will vary and will be readily apparent to those skilled in the art to which the present disclosure belongs (see Remington's Pharmaceutical Sciences, 18th ed., Mack Publishing, Easton PA. (1990)).

A composition containing a pharmaceutically acceptable carrier may be in various formulations such as oral or parenteral formulation. When the composition is formulated, it may be prepared by using conventionally used diluents such as fillers, extenders, binders, wetting agents, disintegrants, and surfactants, or excipients. The carriers, excipients and diluents may be at least one selected from the group consisting of lactose, dextrose, sucrose, sorbitol, mannitol, xylitol, erythritol, maltitol, starchy, acacia rubber, alginate, gelatin, calcium phosphate, calcium silicate, cellulose, methyl cellulose, microcrystalline cellulose, polyvinylpyrrolidone, physiological saline, methyl hydroxybenzoate, propyl hydroxybenzoate, talc, magnesium stearate and mineral oil, dextrin, calcium carbonate, propylene glycol, and liquid paraffin, but are not limited thereto. Any conventional carrier, excipient or diluent may be used. The components may be added independently or in combination with the active ingredient, the virus.

In addition, solid formulations for oral administration may include tablets, pills, powders, granules, capsules, and the like. These solid formulations may be prepared by mixing one or more compounds and at least one of the excipients, for example, starch, calcium carbonate, sucrose or lactose, and gelatin. Also, in addition to a simple excipient, lubricants such as magnesium stearate and talc may be used. Liquid formulations for oral administration include suspensions, liquid solutions, emulsion, and syrup, and may include various excipients, for example, wetting agents, sweeteners, fragrances, and preservatives, in addition to the commonly used simple diluents such as water and liquid paraffin.

Formulations for parenteral administration may include sterile aqueous solutions, non-aqueous solvents, suspensions, emulsions, lyophilizing agents, and suppositories. Non-aqueous solvents and suspension solvents may be vegetable oils such as propylene glycol, polyethylene glycol, and olive oil; and injectable esters such as ethyl oleate. As a base for suppositories, witepsol, macrogol, tween 61, cacao butter, laurinum, glycerol, and gelatin may be used.

In addition, the pharmaceutical composition of the present disclosure may be in any one of the formulations selected from the group consisting of tablets, pills, powders, granules, capsules, suspensions, liquid solutions, emulsions, syrups, sterile aqueous solutions, non-aqueous solvents, suspensions, emulsions, lyophilizing agents and suppositories. As a base for suppositories, witepsol, macrogol, tween 61, cacao butter, laurinum, glycerol, and gelatin may be used.

The pharmaceutical composition of the present disclosure may be administered orally or parenterally (for example, intravenous, subcutaneous, intra-abdominal, or topical administration) according to a desired method, with dosage varying in a wide range depending on the weight, age, gender, health condition, diet, time of administration, method of administration, excretion rate, and severity of disease of a patient.

The pharmaceutical composition of the present disclosure may be used alone or in combination with methods using surgery, hormonal therapy, drug therapy, and biological response modifiers for the prevention or treatment of colorectal cancer.

The composition according to the present disclosure may contain a pharmaceutically effective amount of the virus alone or may contain one or more pharmaceutically acceptable carriers, excipients or diluents. In the above, the pharmaceutically effective amount refers to an amount sufficient to prevent, improve and treat symptoms of immune diseases.

An effective amount of the virus is the amount required, at the dosages and for sufficient time period, to alleviate, improve, mitigate, ameliorate, stabilize, prevent the spread of, slow or delay the progression of or cure the disease.

For example, it may be an amount sufficient to achieve the effect of reducing the number or destroying cancerous cells or reducing the number of or destroying cells chronically infected with a virus, or inhibiting the growth and/or proliferation of such cells.

The effective amount may vary depending on many factors such as the pharmacodynamic properties of the virus, the method of administration, the age, health state and weight of the patient, the nature and extent of the disease state, the frequency of the treatment and the type of current treatment, if any, and the virulence and titer of the virus. Those skilled in the art may adjust an appropriate amount based on the above factors. The virus may be administered initially in an appropriate amount that may be adjusted as required, depending on the clinical response of a patient. The effective amount of a virus may be determined empirically and depend on the maximal amount of the virus that may be administered safely, and the minimal amount of the virus that produces a desired result.

To produce a similar clinical effect when administering the virus systemically to that achieved through injection of the virus at a disease site, administration of significantly higher amounts of a virus may be required. However, the appropriate dose level should be the minimum amount that would achieve the desired result.

The concentration of a virus to be administered will vary depending on the virulence of the virus that is to be administered and on the nature of the cells that are being targeted. Effective amounts of a virus may be given repeatedly, depending upon the effect of the initial treatment regimen. Administrations are typically given periodically, while monitoring any response. It will be recognized by those skilled in the art that lower or higher dosages than those indicated above may be given, according to the administration schedules and routes selected.

An embodiment of the present disclosure provides a method for selecting an H domain that specifically infects a target cancer cell, in which the method includes: producing a mutation H domain by randomly generating a mutation in a gene encoding the H domain of a HN protein of a Newcastle disease virus represented by a nucleotide sequence represented by SEQ ID NO: 8; fusing an avidin protein and the mutation H domain to produce a mutation H domain-avidin fusion protein; treating the target cancer cell with the H domain-avidin fusion protein; and measuring an expression level of the mutation H domain-avidin fusion protein.

In addition, the mutation may be prepared by various methods known in the pertinent field such as an error-prone PCR, a DNA shuffling method, and a site-directed mutagenesis method.

In one embodiment of the present disclosure, the mutation may be prepared by an error-prone PCR (EP-PCR) to make a random mutation. EP-PCR conditions were performed according to the protocol of the EP-PCR kit manufacturer (Agilent Co.), and it was identified that the gene fragments made after performing an EP-PCR were made the same size through agarose electrophoresis.

The mutation H domain-avidin fusion protein may be labeled with a detectable label. For example, the detectable label includes a chemical label (for example, biotin), an enzyme label (for example, horseradish peroxidase, alkaline phosphatase, peroxidase, luciferase, β-galactosidase and β-glucosidase), a radioactive label (for example, C14, 1125, P32 and S35), a fluorescence label (for example, coumarin, fluorescein, FITC (fluoresein isothiocyanate), rhodamine 6G, rhodamine B, TAMRA (6-carboxy-tetramethyl-rhodamine), Cy-3, Cy-5, Texas Red, Alexa Fluor, DAPI (4,6-diamidino-2-phenylindole), HEX, TET, Dabsyl and FAM), a luminescent label, a chemiluminescent label, FRET (fluorescence resonance energy transfer) label or a metal label (for example, gold and silver). For using the detectably labeled MSH2 protein or candidate material, a binding of MSH2 protein with the candidate material may be detected and analyzed through the signal generated by the label. For example, when alkaline phosphatase is used as a label, the signal is detected using a substrate for color developing reactions such as bromo-chloro-indolylphosphate (BCIP), nitro blue tetrazolium (NBT), naphthol-AS-B1-phosphate and ECF (enhanced chemifluorescence). When horseradish peroxidase is used as a label, the signal is detected using a substrate such as chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), YR (p-phenylenediamine-HCL and pyrocatechol), TMB (tetramethyl-benzidine), ABTS (2,2'-Azine-di[3-ethylbenzthiazoline sulfonate]), OPD (o-phenylenediamine) and naphthol/pyronin.

In addition, the measurement of the expression level of the protein may be performed by one or more methods selected from the group consisting of western blot, enzyme linked immunosorbent assay (ELISA), radioimmunoassay (RIA), radioimmunodiffusion, Ouchterlony immunodiffusion, rocket immunoelectrophoresis, histoimmunostaining, immunoprecipitation assay, complement fixation assay, fluorescence-activated cell sorting (FACS), and protein chips, but is not limited thereto.

In one embodiment of the present disclosure, the mutation H domain-avidin fusion protein may be screened for H domain mutants capable of specific binding to cancer cells through the difference in binding ability to the surface proteins of cancer cells through the ELISA method. Specifically, the randomly mutated H domain gene was prepared to be expressed as a recombinant fusion protein by inserting a link peptide in the middle of the avidin protein gene, and the H domain-linker-avidin (H-avidin) gene was inserted into an expression vector (pRSET-A vector). Thereafter, *E. coli* (BL21 strain) was transformed using a heat shock transformation method, and then *E. coli* was spread on a Luria bertani agar plate (containing 100 ug/ml of ampicillin) and cultured overnight in an incubator at 37° C. The colony formed after culture induced protein expression through a known ELISA method. After coating cell plasma protein on an ELISA plate, the bacterial disruption supernatant containing an H domain-avidin protein was reacted, and then a reagent bound with HRP (horseradish peroxidase) was reacted to biotin and a substrate was added to measure the optical density, so that the H domain mutant of the well showing the highest value was selected.

An embodiment of the present disclosure provides a method for preventing or treating colorectal cancer, in which the method includes administering the composition to a subject excluding a human, and a method for providing information for preventing or treating colorectal cancer, in which the method includes: administering the pharmaceutical composition to a subject; and measuring and evaluating changes in cancer cells or cancer tissues of a subject.

Since the method of the present disclosure includes the above-described pharmaceutical composition, the description of the contents overlapping with the above-described pharmaceutical composition of the present disclosure is omitted in order to avoid the excessive complexity of the present specification due to the overlapping description.

The pharmaceutical composition of the present disclosure may be administered in a therapeutically effective amount or in a pharmaceutically effective amount.

As used herein, the term "therapeutically effective amount" refers to an amount of a pharmaceutically acceptable salt of the composition effective for preventing or treating a target disease. The therapeutically effective amount of the composition of the present disclosure may be determined by considering various factors such as an administration method, a target area, and a patient condition. Thus, when used in the human body, the dosage should be determined as an appropriate amount in consideration of both safety and efficiency. It is also possible to estimate the amount used in humans from the effective amount determined through animal experiments. These factors in determining effective amounts are described, for example, in Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), and Mack Publishing Co.

As used herein, the term "pharmaceutically effective amount" refers to an amount sufficient for the treatment of diseases at a reasonable benefit/risk ratio applicable to a medical treatment without causing any adverse effects, and the level of the effective dose may be determined based on the factors including the health conditions of a patient, type of disease(s), severity of illness, drug activity, sensitivity to drug, administration method, administration time, administration route and excretion rate, duration of treatment, factors including drug(s) to be mixed or concurrently used in combination, and other factors well known in the medical field. The composition of the present disclosure may be administered as an individual therapeutic agent, in combination with other therapeutic agents, or sequentially or simultaneously with conventional therapeutic agents, and may be administered once or multiple times. It is important to administer the composition in an amount to obtain the maximum effect with a minimum amount without adverse effects considering all of the factors described above, which may be easily determined by those skilled in the art.

An embodiment of the present disclosure provides a method for evaluating an effect of preventing or treating colorectal cancer in animals, in which the method includes administering the pharmaceutical composition to an animal excluding a human.

In addition, the method may be evaluated by measuring changes in cancer cells or cancer tissues in animals excluding humans.

In addition, the therapeutic effect is verified by a reduction or absence of clinical manifestation normally exhibited by colorectal cancer, a faster recovery time or a lower duration, a difference in a low number of brain tumor cells in samples of blood, body fluids or organs of brain tumor cells, a reduction of brain tumor tissues, and a death of brain tumor cells.

In addition, the effective amount of the therapeutic agent means an amount capable of inducing the effect of inducing a therapeutic effect, such as reduction of clinical symptoms caused by colorectal cancer in humans, reduction of cancer cells, reduction of cancer tissue, etc., and may be appropriately selected by those skilled in the art. For example, in the case of an effect amount of a therapeutic agent containing a recombinant viral composition, an amount of the purified virus may be $10^{5.0}$ $TCID_{50}$/ml to $10^{11.0}$ $TCID_{50}$/ml. More preferably, it may be $10^{8.0}$ $TCID_{50}$/ml to $10^{9.0}$ $TCID_{50}$/ml or more.

An embodiment of the present disclosure provides a method for producing a recombinant Newcastle disease virus (Accession No. KCTC14630BP), in which the method includes: inoculating the recombinant Newcastle disease virus into a host cell line; culturing the host cell line; and obtaining the recombinant Newcastle disease virus (Accession No. KCTC14630BP) from a culture of the host cell line.

In the present disclosure, the recombinant Newcastle disease virus (Accession No. KCTC14630BP) may be recovered through a conventional virus production method. Three types of helper plasmids (NP, P, L) and modified vaccina virus (MVA/T7) were injected into the HEp-2 cell line and cultured, followed by the recovery of the recombinant virus according to a conventional method. Transfection was performed using lipofectamine 3,000 as an injection method into the cell line, and HEp-2 cells were used as the cell line. After culturing for 3 to 4 days, the recombinant virus was recovered and inoculated into the allantoic cavity of an 8 to 10 day old SPF embryonated egg. After culturing the virus, the allantoic fluid was recovered and the virus titer was increased by culturing at least two blind passages on embryonated eggs in the same way. After purification from the allantoic fluid by a conventional purification method, it was cultured in Vero76 cells selected as an appropriate cell line and used in the experiment.

Purification of the virus proceeds clarification by centrifugation after harvesting the recombinant virus culture. Clarification may be performed by centrifugation or microfiltration. The centrifugation may be performed under the conditions of 10,000 g, 10 minutes, and 4° C. so that supernatants may be used for the next purification process. In the case of microfiltration, a filter with a pore size of 1.0 μm to 0.2 μm may be used, and a filter with a pore size of 0.45 μm may be preferably used. As the filtration method, either dead end filtration or cross flow filtration may be used, and both methods are applicable. Recombinant virus purification is possible through known methods, including extraction through chromatography or ultrafiltration method. Additional virus purification is recovered by precipitating or separating the virus by ultra-high-speed centrifugation using sucrose gradient media, and the recovered virus is resuspended in TNE buffer for use in the next process. In the purification method using chromatography, virus purification is possible through a combination of appropriate resin and buffer through a difference in binding power such as affinity, ion exchange, size exclusion, and hydrophobic. Preferably the size exclusion chromatography method will be appropriate. Recombinant viruses were purified using size exclusion chromatography, and after sample loading, absorbances at 260 nm and 280 nm were measured to select virus-containing fractions and used in the next process. The recovered fraction was recovered by precipitating or separating the virus by ultra-high speed centrifugation using sucrose gradient media, and the recovered virus was resuspended in physiological saline for injection and used in the experiment. Experiments on the cell infectivity of the purified virus were conducted on the infectivity and proliferation power of various cancer cells and normal cells according to various MOI conditions. The cell line that may be used for such an experiment may be various mammalian cell lines and cancer cells developed to date, and preferably a cancer cell line. Cancer cell lines that may be used are selected from the group consisting of T98G, HT-1197, RT-4, SW780, A673, Saos-2, SK-PN-DW, A172, Daoy, SW1108, HCC-38, BT-549, DU4475, SW1116, LS123, LoVo, COL0205, HT-29, SW480, SW620, Hela, SW626, PA-1, ME-180, THP-1, MOLT-4, C3A, SNU387, NCI-H1299, A549, NCI-H1770, NCI-H1882, CSA46, SU-DHL-2, Capan-2, HPAF-II, A375, SH-4, GCT, SNU-16, and AGS. In addition, newly established cancer cell lines may also be used without limitation.

Hereinafter, the Examples of the present disclosure will be described in more detail with reference to the accompanying drawings. However, the following Examples are only intended to embody the contents of the present disclosure, and the present disclosure will not be limited thereto.

<Example 1> Production of Recombinant NDV Virus (LVP-K1) Genome Vector Using NDV VG/GA Strain as Basic Backbone NDV VG/GA has about 15 kb of negative-sense single-stranded RNA as genetic information and is composed of 6 ORFs, and the proteins that form a structure of the virus encode NP, P, M, F, HN and L genes. After RNA isolation using a viral RNA extraction kit (Qiagen), five pairs of primers specific to each gene were prepared and reverse transcription polymerase chain reaction (RT-PCR) was performed. Five pairs of primers specific to the gene are shown in Table 1 (showing the primers used during the insertion process using a restriction enzyme into a pBR322 vector after cDNA synthesis of the present disclosure). RT-PCR was performed at 42° C. for 1 hour and at 94° C. for 5 minutes, followed by a total of 30 cycles of 94° C. for 1 minute, 60° C. for 1 minute, and 72° C. for 1 minute, followed by reaction at 72° C. for 7 minutes. A cloning strategy for serially linking a set of cDNA fragments of four fragments is shown in FIG. 1.

FIG. 1 shows an insertion process into a modified pBR322 vector by synthesizing a NDV VG/GA strain of the present disclosure with cDNA. Cloning was performed by locating six cDNA fragments generated by RT-PCR with the modified pBR322 vector, which is a modified low-copy-number plasmid, with PacI and PmeI restriction enzymes having different recognition sites and cleavage sites. The modified pBR322 vector was under the control of a T7 RNA polymerase promoter, and was located so that it was terminated by the hepatitis delta virus (HDV) antigenome ribozyme and T7 terminator gene used to split RNA at the terminus of the NDV genome to enable viral encapsidation and packaging. In addition, the complete genome sequence of the NDV VG/GA strain was included to ensure accurate transcription.

In order to increase the reconstitution efficiency of the vector, cloning was performed by locating PacI and PmeI restriction enzymes having different recognition sites and cleavage sites into a modified pBR322 vector, which is preferably a low-copy-number plasmid. The modified pBR322 vector was preferably under the control of a T7 RNA polymerase promoter, and was located so that it was terminated by the hepatitis delta virus (HDV) antigenome ribozyme and T7 terminator gene used to split RNA at the terminus of the NDV genome to enable viral encapsidation and packaging. In addition, the complete genome sequence of the NDV VG/GA strain was included to ensure accurate transcription. The produced virus was named LVP-K1 virus.

RNA-dependent RNA polymerase initiates transcription in a sequential manner by the stop-start mechanism IGS (GE-IG-GS) between genes. In GS, the transcriptional reinitiation is not complete, so the level of transcription of mRNA located at the 3' terminus is high. Accordingly, the closer the 3' terminus, the higher the mRNA transcription level, and the level decreases as it goes towards the 5' terminus. Accordingly, a new foreign gene insertion between the NP gene and the P gene results in a higher level of mRNA transcription and foreign protein translation than between the P gene and the M gene and between the HN gene and the L gene, and thus the gene insertion between NP and P genes is more preferable.

TABLE 1

| Gene | Direction | Sequence (5'→3') | Restriction site | SEQ ID NO. |
|---|---|---|---|---|
| Fragment 1 (L2) | Forward | ACGCGTggtctcaggtttatatgcagggaa | MluI | 9 |
|  | Reverse | TTAATTAAaccaaacaaagatttggtgaatg | PacI | 10 |
| Fragment 2 (L1) | Forward | ACTAGTtgagattctcaaggatgatgggt | SpeI | 11 |
|  | Reverse | ACGCGTcgagtgcaagagactaatagtttt | MluI | 12 |
| Fragment 3 (F-HN) | Forward | GGCGCCattatcggtggtgtagctctcgg | Kas I | 13 |
|  | Reverse | ACTAGTaaagggacgattctgaattccccg | SpeI | 14 |
| Fragment 4 (P-M-F) | Forward | CCGCGGaaacagccaagagagaccgcagaa | SacII | 15 |
|  | Reverse | GGCGCCaaccgggatccagaatcttctacccgt | Kas I | 16 |
| Fragment 5 (NP-P) | Forward | GTTTAAACaccaaacagagaatccgtaagg | PmeI | 17 |
|  | Reverse | CCGCGGctttgttgactcccctgttgttga | SacII | 18 |

<Example 2> H Domain and Avidin Fusion Protein Expression 2-1. Cancer Cell Specific Binding Identification Test Using Purified H Domain Mutation-Avidin Protein The viral surface HN protein is an important antigen responsible for viral attachment to the sialic-acid receptor. HN plays an important role in the entry of viral RNA into cells by promoting membrane fusion through interaction with the F protein. HN is a type II homotetrameric membrane protein and consists of an N-terminal transmembrane domain, a linear protein domain, and a C-terminal globular head domain. Linear proteins mediate the interaction between HN and F proteins and affect fusion activity. Globular head domain (H domain) is a major functional domain of HN protein and contains receptor binding sites known as "site I" and "site II." Site I is associated with sialic-acid receptor binding and neuraminidase activity, and site II is associated with fusion-related receptor binding and fusion. In other words, the sialic acid binding domain of HN protein plays a very important role in tissue tropism of NDV infection.

Directed evolution refers to a process of selecting a protein having a desired function by intentionally inducing a mutation with a technique for changing a nucleotide sequence by mimicking the natural selection process used in protein engineering. In other words, to improve the cancer cell affinity of the globular head domain gene of the HN protein to the sialic-acid receptor of the host cell, EP-PCR (Error prone PCR, GeneMorph II Random Mutagenesis kit, Agilent Technologies) was performed, and then the random point mutant HN-avidin gene was amplified together with the avidin gene to identify the presence of water-soluble protein using the *E. coli* expression system (see FIGS. 2 to 4).

FIG. 2 is a diagram schematically showing the application of directed evolution technology for the construction of an H domain protein with improved binding ability to cancer cells, and briefly shows a method for making various mutants using the EP-PCR technology for H domain genes and screening for mutants with increased affinity for cancer cell surface proteins.

FIG. 3A is a schematic diagram of a gene configuration constructed with a fusion protein by linking the mutation H domain gene and avidin gene with the linker peptide gene using EP-PCR to screen the mutation H domain by ELISA method.

FIG. 4B shows the expression of an S519G mutation H domain protein, which shows the highest O.D value for the HCT116 cancer cell surface protein through an ELISA screening method.

The H domain is a sialic acid binding domain located at positions 123 to 571 of the amino acid sequence of the HN protein (UniProt Acc. No. P13850), and a codon-optimized gene for *E. coli* was synthesized using the H domain gene and the avidin gene. Precisely, the H domain gene was linked to the avidin gene using a Bam HI restriction enzyme site located at the 5' end of the linker peptide gene and the H domain gene and a Sbf1 restriction enzyme site located at the 3' end of the avidin gene. A linker peptide was inserted between the H domain protein and the avidin protein to avoid structural interference as much as possible. The H domain and avidin fusion protein genes were amplified using PCR using primer sets (HN opti EP PCR F:5'-TGT GGT GCG CCA ATT CAT G-3' (SEQ ID NO: 19), HN opti avidin PCR R:5'-TTA CTC CTT CTG GGT GCG CAG-3' (SEQ ID NO: 20)). In order to introduce the H domain and the avidin gene fragment into the vector, T4 ligase was incubated at 4° C. overnight to ligate two DNA fragments. The H domain-avidin vector (FIG. 3A) constructed by the above method was introduced into transformable *E. coli* cells by heat shock at 42° C. for 1 minute. The transformed *E. coli* was cultured overnight at 37° C. in a medium (100 ug/ml) containing ampicillin. The formed colonies were inoculated with LB liquid, and 0.1 M isopropyl b-D-1-thiogalactopyranoside (IPTG) was added when the $OD_{600}$ measured value became 0.4. After IPTG induction, samples were cultured at 27° C. for 6 hours and collected every hour. Five samples were centrifuged at 9,000 g for 10 minutes to obtain a pellet. The *E. coli* pellet was homogenized with a sonicator, resuspended in PBS, and centrifuged at 9,000 g for 10 min. After separating the supernatant (Sup) and the pellet, the presence of water-soluble protein was identified by western blotting (FIG. 4B). For western blotting, a His-tag-horseradish peroxidase conjugate antibody that specifically binds to His-tag protein was diluted to 1/5,000 and used. However, the concentration of the His-tag-horseradish peroxidase conjugate antibody used is not limited to 1/5,000. The above supernatant was used to screen for colorectal cancer cell-specific proteins.

2-2. Experiments on Binding and Specificity of H Domain Mutation-GFP Protein to Cancer Cell Surface For the experiments to identify the HCT116-specific binding of the H-domain mutation-GFP protein using various cancer cells, comparison tests were performed on various cancer cells and normal cells in addition to the HCT116 cell line. HCT116, T98G, and A549 cells were used for cancer cells, and CCD-18Co cells were used for normal cells.

Figure 5A:
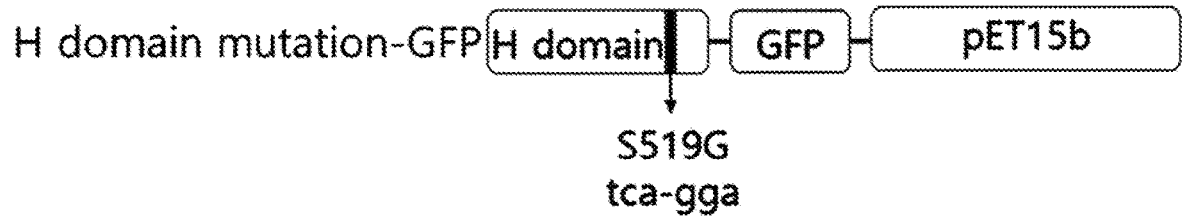
FIGS. 5A-5C are schematic diagrams of a plasmid of a mutation H domain (S519G)-GFP fusion protein, and the results of purification using ion exchange chromatography, and the results of surface binding analysis of various cancer cells and colorectal normal cells.

H domain and green fluorescence protein (GFP) were linked with a linker peptide to observe whether the H domain mutant was bound to the cancer cell surface and whether there was a change such as specific binding to a specific cancer cell or an increase in binding ability (affinity increase). Thus, the expression was purified through the *E. coli* expression system. For the H domain gene, the mutation H domain gene selected through the experiments above was used. For the GFP gene, a gene was constructed through codon optimization to be suitable for *E. coli* expression using the enhanced green fluorescent protein (EGFP) gene. For the constructed gene, the gene was inserted into the *E. coli* expression vector plasmid pET15b to construct an expression vector (FIG. 5A). *E. coli* forming colonies through selection media culture (LB agar media, 10 ug/ml of ampicillin) was picked to select *E. coli* transformed with the constructed expression vector by a conventional *E. coli* heat shock transformation method, cultured in liquid media (LB media, 10 ug/ml of ampicillin), mixed with glycerol 20%, and frozen at −70° C. *E. coli* transformed with the pET15b plasmid vector was inoculated into LB broth medium (10 ug/ml of ampicillin). After culturing until the value of O.D. 600 nm became 0.4, IPTG 0.1 M was added to the medium to induce protein synthesis. Thereafter, the culture temperature was lowered from 37° C. to 28° C. to inhibit the production of insoluble proteins. In culture conditions for H domain mutation-GFP protein production, the IPTG induction period (bacterial culture O.D.), the concentration of IPTG, and the setting of the temperature after IPTG addition are not limited to the above conditions, but may vary according to the optimal conditions for protein expression. *E. coli* whose protein expression had been terminated was harvested and centrifuged (6,000 g, 10 minutes, 4° C.). The precipitated cells were resuspended in PBS buffer, and the cells were disrupted using a sonicator. The disrupted cell solution (8,000 g, 10 minutes, 4° C.) was centrifuged. After centrifugation, the supernatant was treated with ammonium sulfate up to 30% to 70% by concentration to separate the precipitated protein and the supernatant. The highest concentration and fraction of H domain mutation-GFP protein were determined through SDS-PAGE and western blotting experiments. The results are shown in FIGS. 5B and 5C.

Figure 5B:
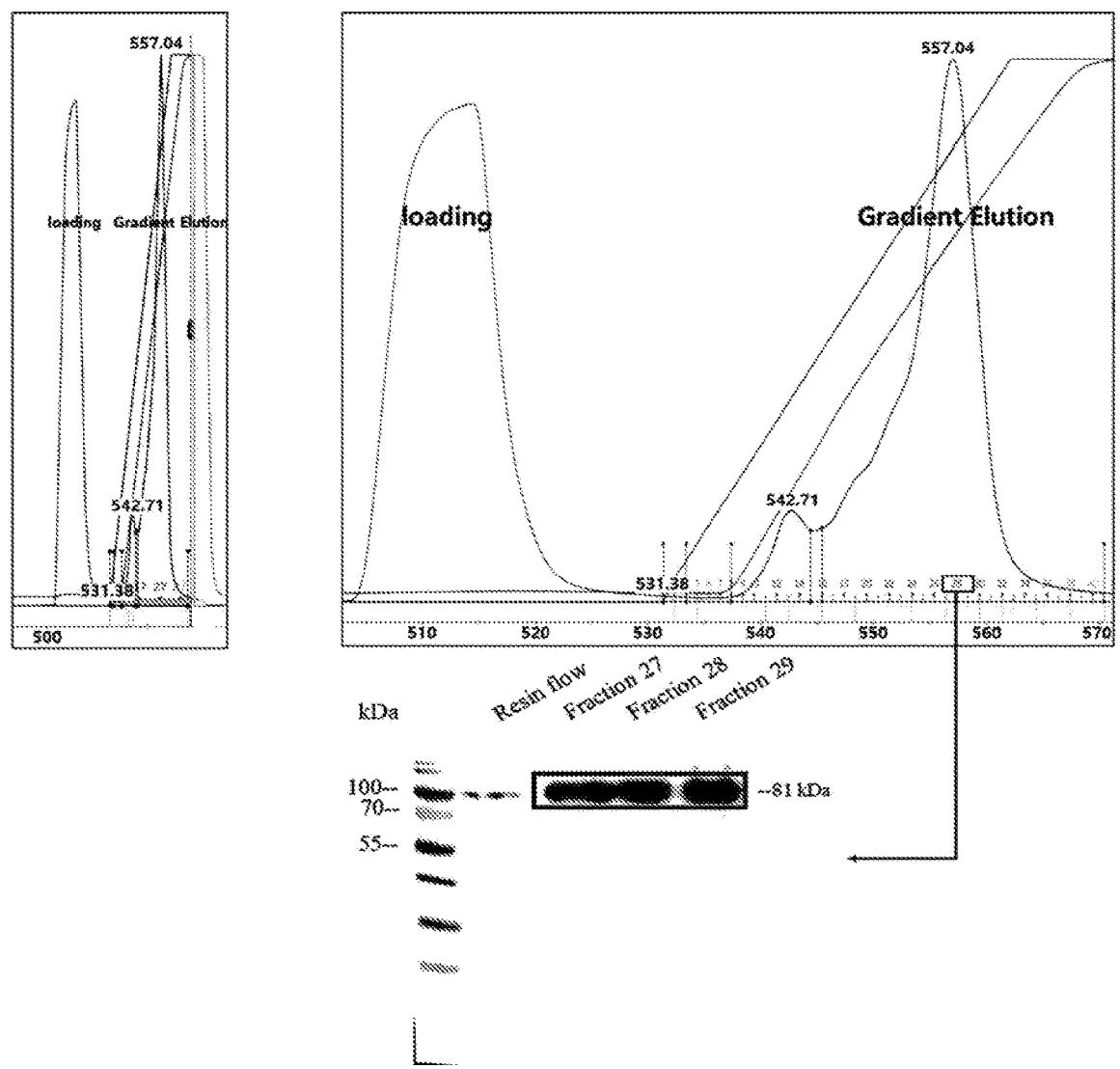
Figure 5C:
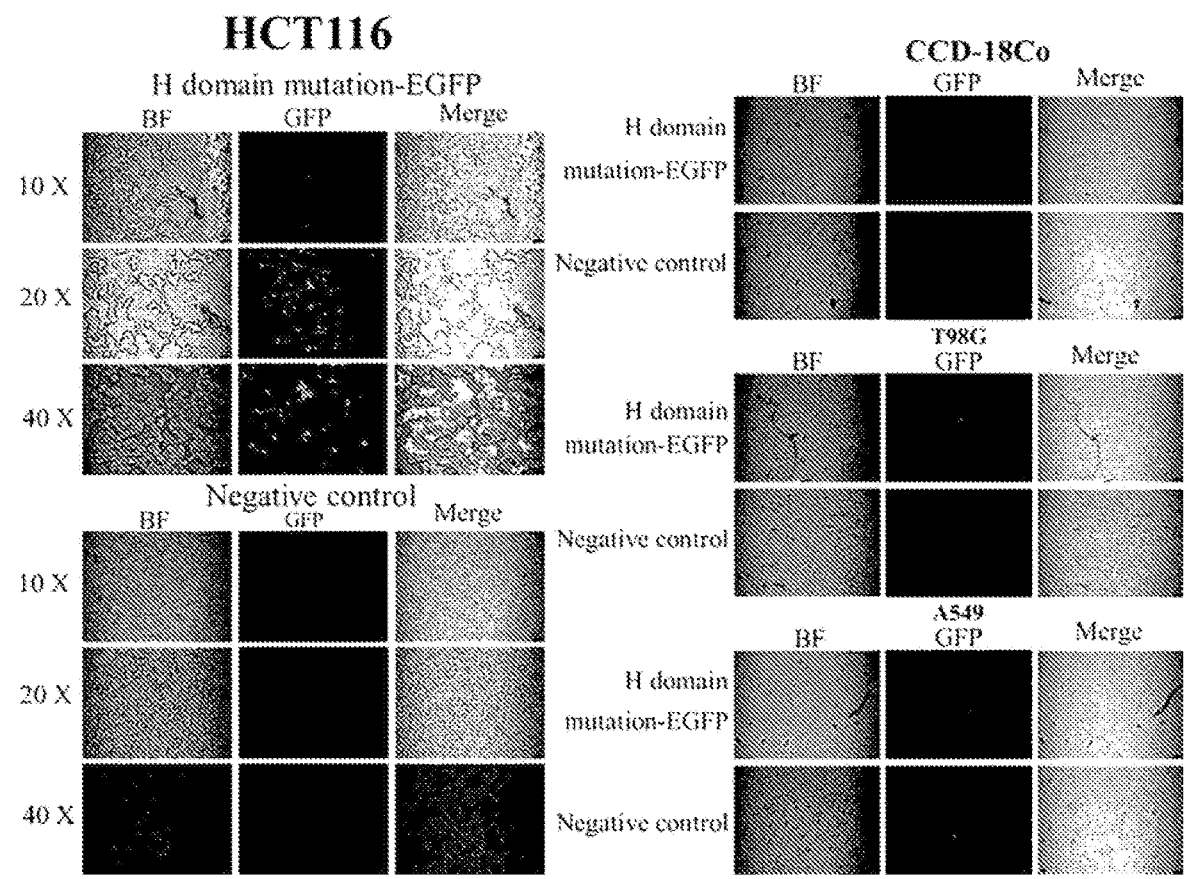

FIG. 5B shows the results identified by performing western blotting and a chromatogram showing the results of purification using ion exchange chromatography of the mutation H domain (S519G)-GFP fusion protein. FIG. 5C shows the results of identifying the surface binding of various cancer cells (HCT116: colorectal cancer, T98G; glioblastoma, A549; lung cancer) and colorectal normal cells (CCD-18Co) of a mutation H domain (S519G)-GFP fusion protein for various cancer cells using a fluorescence microscope.

As a result, as a result of observing each well under a microscope, HCT116 cells showed the greatest number of fluorescence. It was not observed that the H domain mutation-GFP protein showed unusually high fluorescence among other cells. It may be anticipated from these results that the mutation H domain has increased binding ability to the surface proteins of HCT116 cells and that the range of surface proteins that may be bound has been expanded.

<Example 3> Selection of H Gene with Improved Binding Ability to Colorectal Cancer (Tropism)

The improvement of colorectal cancer cell affinity was selected by a general ELISA method using HCT116 cells. HCT-116 cells were cultured according to the basic cell culture method. After centrifugation at 3,000 g at 4° C. for 10 minutes, the cells were resuspended in the buffer provided by the ab65400 Plasma Membrane Protein Extraction Kit (Abcam. Co.) to separate cancer cell surface proteins. Protein separation was performed according to the protocol provided by the manufacturer, and the protein concentration of the separated supernatant was measured by the lowry method. After coating the cancer cell lysates at a protein concentration of 50 ug/ml in a 96-well plate overnight at 4° C., on the next day, in order to remove unbound cancer cells, the cells were washed with a water washing solution (Tris buffer (pH 8.0 tween 0.2%)). The cells were blocked with 1% bovine serum albumin (BSA) at room temperature for 1 hour. In order to screen for the point mutant HN-avidin protein, the cells were reacted at a concentration of 50 ug/ml at 37° C. for 1 hour. Thereafter, the cells were reacted with biotin-horseradish peroxidase (HRP) 1/1,000 at 37° C. for 1 hour, and then washed 3 to 6 times with a water washing solution. A tetramethyl benzidine (TMB) peroxidase substrate was added to the plate. The plate was reacted at room temperature for 10 minutes. When the color started to change, the absorbance was measured at 450 nm (FIG. 3B).

Figure 3A:
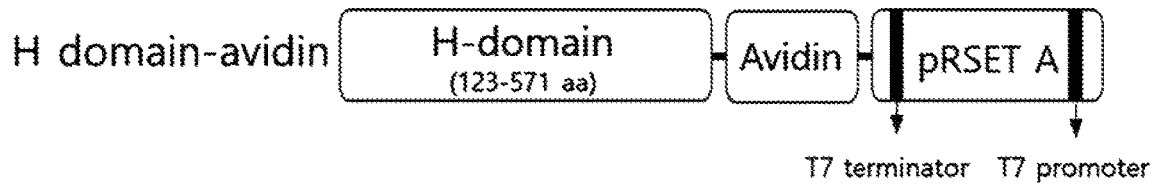
FIG. 3A is a schematic diagram of a gene configuration constructing a fusion protein by linking the mutation H domain gene and avidin gene with the linker peptide gene using EP-PCR to screen the mutation H domain by ELISA method.
Figure 3B:
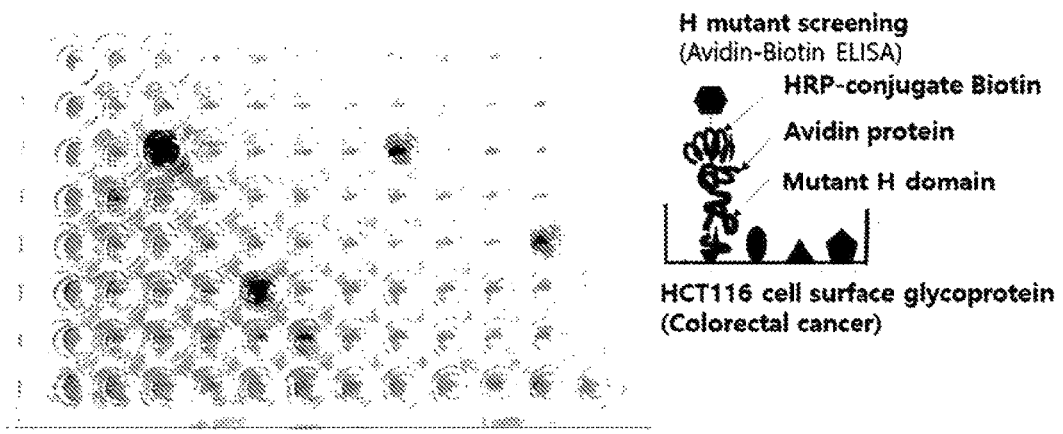
FIG. 3B is a diagram showing the results of screening a protein with high binding ability to colorectal cancer cells by ELISA using an H domain-avidin binding protein.

FIG. 3B exemplarily shows the results of screening a total of 50 plates by an ELISA method for a protein having high binding ability to colorectal cancer cells (HCT116) using an H domain-avidin binding protein.

Among a total of 50 plates, gene sequencing of five strains with high OD values at O.D. 450 nm was analyzed.

As a result of sequence analysis, it was found that in each of the five mutation H domains, a mutation occurred in which TCA (serine) of the amino acid sequence at a position 519 of the H domain represented by SEQ ID NO: 8 was substituted with GGA (glycine) (SEQ ID NO: 3, C3 of plate No. 7 of FIG. 3B), CCC (proline) of the amino acid sequence at a position 267 was substituted with GGC (glycine), GGG (glycine) at a position 486 was substituted with GGA (glycine) (SEQ ID NO: 4, A6 of plate No. 13), GCT (alanine) of the amino acid sequence at a position 182 was substituted with GAT (aspartic acid), CTC (leucine) at a position 566 was substituted with CTT (leucine) (SEQ ID NO: 5, H9 of plate No. 22), TCA (serine) of the amino acid sequence at a position 418 was substituted with CCA (proline), ACA (threonine) at a position 528 was substituted with ACT (threonine) (SEQ ID NO: 6, E3 of plate No. 30), GGG (glycine) of the amino acid sequence at a position 319 was substituted with GCG (alanine), CCC (proline) of the amino acid sequence at a position 325 was substituted with CGC (arginine), and CCC (proline) of the amino acid sequence at a position 392 was substituted with CAC (histidine) (SEQ ID NO: 7, F8 of plate No. 47), respectively.

Figure 4A:
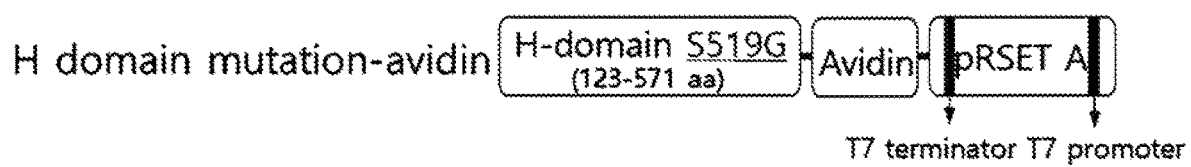
FIGS. 4A-4D are schematic diagrams of the H-domain mutation-avidin protein in which the amino acid sequence of the mutation H domain (S519G) is substituted, and a gel photograph showing purification using Western blot and an ion exchange chromatography, and the results of ELISA experiments for surface proteins of various cancer cells and colorectal normal cells.
Figure 4B:
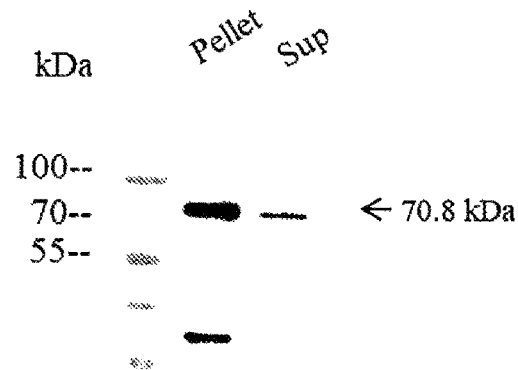

Among them, for the gene sequence of the mutation H domain of the strain with the highest OD value, the nucleotide sequences represented by SEQ ID NO: 8 at positions 1555 and 1556 corresponding to the H domain of the LVP-K1 vector were substituted from TC to GG. For the amino acids, it was identified whether TCA (serine) was changed to GGA (glycine) (FIG. 4A). FIG. 4A shows a schematic diagram of the H-domain mutation-avidin protein in which the amino acid sequence (S519G) of the mutation H domain was substituted.

<Example 4> Purification of H Domain-Avidin Fusion Protein with Improved Binding Ability to Colorectal Cancer (Tropism) and Characterization In order to identify the binding ability between the mutation H domain (SEQ ID NO: 3)-avidin fusion protein and cancer cells, the mutation H domain-avidin protein was purified. AKTA pure (GE healthcare) equipment and Hitrap SP FF 5 ml column, a cation exchange resin, were used. For purification, 20 mM HEPES buffer (pH 6.5) and 20 mM HEPES buffer (pH 6.5) containing 1 M NaCl were used. The column connected to AKTA pure was washed in the order of 20% ethanol, distilled water, and 20 mM HEPES buffer (pH 6.5), and the protein sample to be purified was loaded at a flow rate of 1 min/ml. While checking the peak measured at 280 nm, the resin flow was received when the peak was on the rising curve, and when loading was completed, the non-binding protein in the resin was washed with 20 mM HEPES buffer (pH 6.5). When the peak was stabilized, gradient elution was performed using 20 mM HEPES buffer (pH 6.5) containing 1 M NaCl for 30 minutes in 1 ml fraction at a flow rate of 1 min/ml. The purification result was identified by performing western blotting using the fraction collected at the center of the peak measured at 280 nm (FIG. 4C).

Figure 4C:
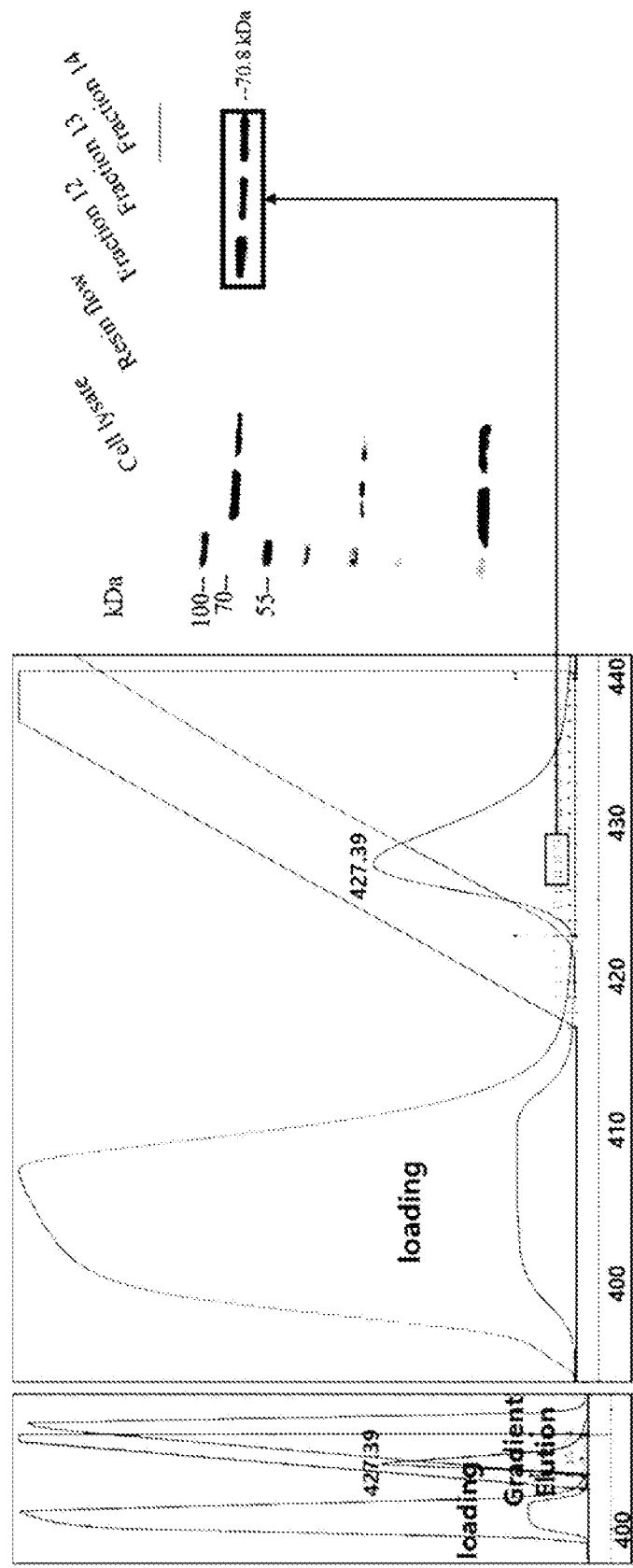

FIG. 4C shows the results of purification of the S519G mutation H domain protein using ion exchange chromatography.

Figure 4D:
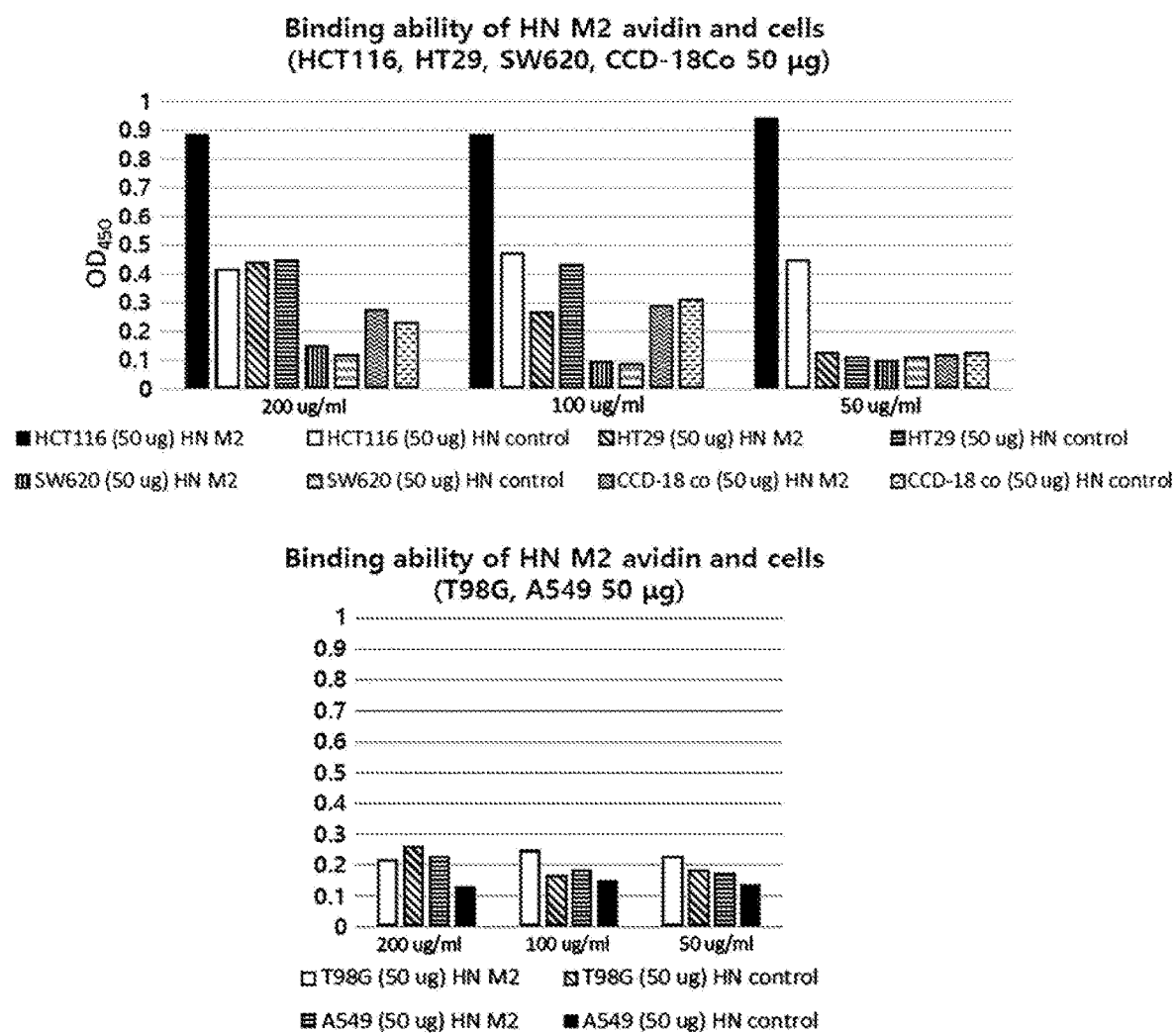

For the H-domain mutation-avidin protein purified by the above method, the binding ability of the H-domain mutation-avidin protein was identified in colorectal cancer cells (HCT116, SW620, HT29), colorectal normal cells (CCD18-Co), other cancer cells (A547; lung cancer, T98G; glioblastoma) and normal cells (MRC-5; lung normal cells), and the results are shown in FIG. 4D.

FIG. 4D shows the results of ELISA experiments on the surface proteins of various cancer cells (HCT116, HT29, SW620: colorectal cancer, T98G; glioblastoma, A549; lung cancer) and colorectal normal cells (CCD-18Co) of the S519G mutation H domain protein.

Each cancer cell line and normal cell line was cultured using a medium recommended by ATCC. Cell culture was carried out for 2 to 3 days in a CO2 incubator at 37° C. using a 75T flask. When a full monolayer was formed, the cells were harvested and resuspended in the buffer provided by the ab65400 Plasma Membrane Protein Extraction Kit (Abcam. Co). Each cell surface plasma protein was isolated according to the protocol provided by the company. Each cell plasma protein was quantified by the lowry method, and was prepared by diluting the protein concentration in a 96 well plate to 50 ug/ml with Tris buffer (pH 8.0) for the ELISA experiment. 100 μl of protein was dispensed, incubated at 4° C. overnight, and then the solution was removed. After removing the solution, 200 μl of Tris buffer containing 0.10% tween 20 was dispensed into each well and the removal process was repeated 3 to 6 times to wash the plates. Thereafter, 100 μl of Tris buffer (pH 8.0) containing 1% bovine serum albumin was dispensed into ELISA plate wells and the blocking process was performed at room temperature for 1 hour. After removing the blocking solution, the purified H-domain mutation protein solution was diluted with Tris buffer (pH 8.0) at a concentration of 50, 100, and 200 ug/ml to be 100 μl each and dispensed into each well. After the reaction for 1 hour at room temperature, the solution was removed. 200 μl of Tris buffer (pH 8.0) containing 0.1% tween 20 was dispensed into each well and the removal process was repeated 3 to 6 times to wash the wells. Thereafter, 100 μl of biotin-labeled horseradish peroxidase protein solution diluted 1,000 times was added to each well and reacted at 4° C. for 1 hour. After removing the added solution, the well was washed 3 to 6 times with ELISA washing solution, then 50 μl of 3,3',5,5'-tetramethylbenzidine (TMB) solution was added to proceed with production, and then 50 μl of stop solution (1.0 M $H_2SO_4$) was added to stop the reaction and $O.D._{450\ nm}$ was measured and compared.

As a result, the highest OD value was identified in HCT116 50 ug/ml. It was identified that it showed the lowest binding ability to lung cancer and normal lung cells. These results may support the improved binding ability specifically to colorectal cancer cells.

Figure 6A:
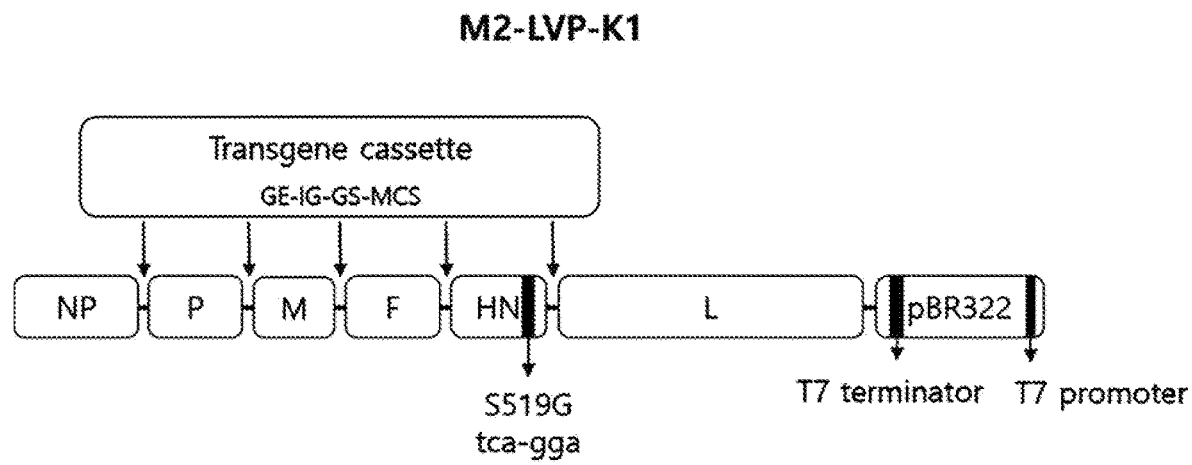

<Example 6> Production of HN Protein-Modified NDV (M2-LVP-K1) with Increased Cancer Cell Specificity The LVP-K1 vector was inserted into the pBR322 vector by obtaining an insert gene of 1,499 bp from 189 bp to 1,688 bp using XbaI and SpeI restriction enzymes. Thereafter, the mutation H domain gene was purified by using a primer (Forward 5'-GGT GAG TGG AAG CAG CAC CAA G-'3 (SEQ ID NO: 21), Reverse 5'-CGG GTT ATG CGA CTG CGG G-'3 (SEQ ID NO: 22)) to obtain a PCR product. T4 kinase (NEB) was treated according to the manufacturer's recommendations, and then reacted at 16° C. using T4 ligase, mutation H domain gene (SEQ ID NO: 3) was introduced into the pBR322 vector into which the insert gene of 1,499 bp of the LVP-K1 vector was inserted, and transformed into *E. coli*, and colonies were obtained using LB agar (100 ug/ml ampicillin). After the obtained colonies were obtained through plasmid preparation, whole nucleotide sequence analysis was performed to identify whether TCA was changed to GGA. Through the same process as described above, an M2-LVP-K1 vector in which the serine corresponding to amino acid sequence at a position 519 of the HN gene of the LVP-K1 vector was substituted with glycine was obtained (FIG. 6A). A transgene cassette may be inserted between the NP and P genes, between the P and M genes, between the M and F genes, between the F and HN genes, and between the HN and L genes of this vector. The transgene cassette includes an IGS sequence (gene end (GE), intergenic sequence (IG), gene start (GS)) and a multicloning site (MCS) nucleotide sequence having a DNA restriction enzyme sequence.

Figure 6B:
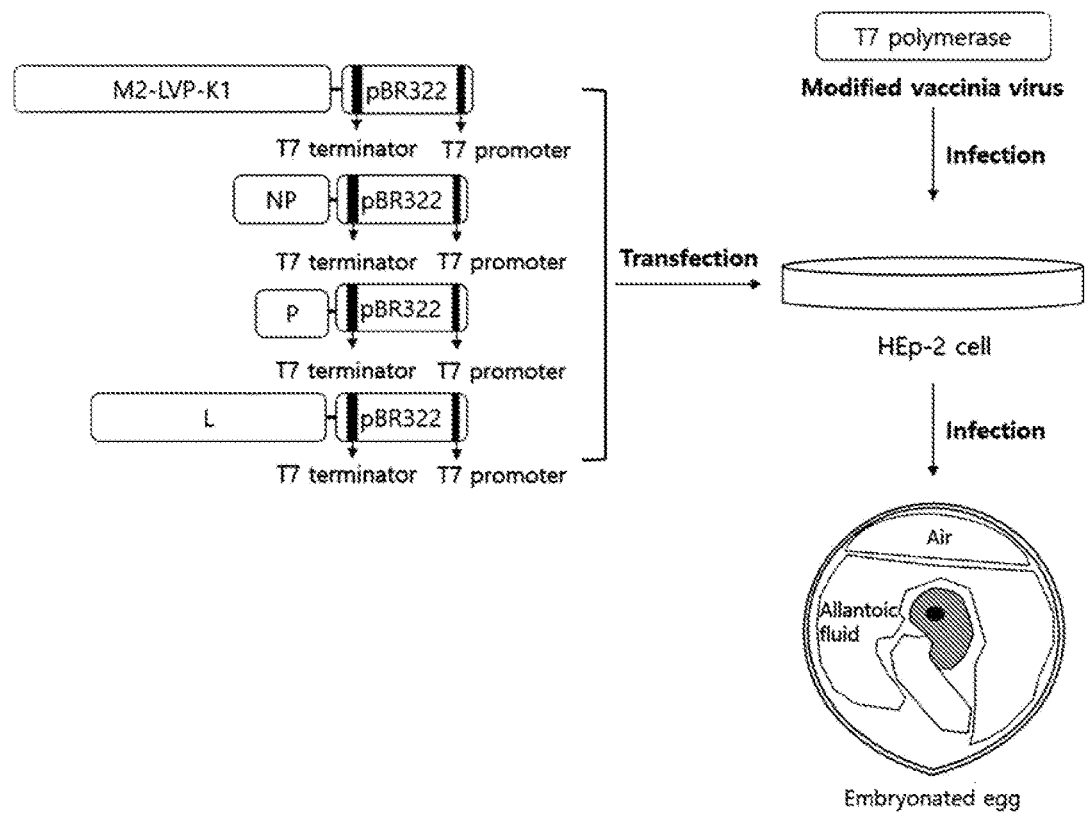

Individual clones (NP, P, L) of the NDV transcriptase complex were cloned into pBR322 vector and used as helper plasmids (pBR322-NP, pBR322-P, pBR322-L). On the previous day, HEp-2 cells were prepared at $5 \times 10^5$ cells/well in a 6-well plate, and the modified vaccinia virus (MVA-T7) was infected at 1 MOI. In the cell line, each of 2.5 μg, 1.5 μg, 0.5 μg, and 5 μg of pBR322-NP, pBR322-P, pBR322-L helper plasmid and M2-LVP-K1 vectors expressing proteins by the T7 promoter were transformed by mixing them with lipofectamine 3000 (Invitrogen) at an appropriate ratio. Thereafter, the HEp-2 cell supernatant was harvested after culture at 37° C. and 5% $CO_2$ conditions for 3 to 4 days. Then, 9 to 11 days old SPF embryonated eggs were inoculated into the allantoic cavity, and allantoic fluid was collected 4 days after inoculation. In order to remove the vaccinia virus, the allantoic fluid diluted at $10^{-3}$ with PBS was inoculated into the allantoic cavity of 9 to 11 days old SPF embryonated eggs, respectively, and the allantoic fluid was collected 4 days after inoculation to conduct a virus identification experiment (see FIG. 6B).

For the virus identification experiment, after isolation of the allantoic fluid using a Viral RNA extraction kit (Qiagen), 5 μl of the extracted RNA and 1 μl of each of the forward and reverse primers in Table 3 below were used for reaction at 42° C. for 1 hour and at 94° C. for 5 minutes with ONE-STEP RT-PCR. Thereafter, a total of 35 cycles of reaction were carried out at 94° C. for 1 minute, at 60° C. for 1 minute, and at 72° C. for 1 minute, and then at 72° C. for 7 minutes for identification. The results are shown in FIG. 6C.

After removing the vaccinia virus, for detecting the gene of the NDV virus in the recovered LVP-K1 and M2-LVP-K1 viruses using an SPF egg, RT-PCT was performed to identify the electrophoresis result, being shown in FIG. 6C.

As a result, the vaccinia virus was removed, and Newcastle disease virus and recombinant Newcastle disease virus LVP-K1 virus and M2-LVP-K1 virus were identified.

LVP-K1 virus titer was $10^{6.7}$ TCID$_{50}$/ml and the M2-LVP-KI virus titer was $10^{6.3}$ TCID$_{50}$/ml.

Median death time (MDT) was measured according to a commonly known method. As a control group, the same concentration of LVP-K1 virus was also measured. The titers of the two viruses were adjusted and used as the same titer as $10^{6.3}$ TCID$_{50}$/ml. The virus undiluted solution was diluted in decimal notation, 0.2 ml of each diluted solution was inoculated into the allantoic cavity of 5 SPF hatching eggs (9 to 11 days old), and then cultured in a hatching egg incubator (Ari 50) at 37° C. for 5 days. The mortality of the

TABLE 2

| Gene | Direction | Sequence (5'→3') | Size (bp) | SEQ ID NO. |
|---|---|---|---|---|
| NDV check | Forward | CCACAATTCCAAGATAACCGGAG | 327 | 23 |
|  | Reverse | GCTGCCACAATCAGATGCCTTTG |  | 24 |
| Vaccinia virus check | Forward | ATGACGATGAAAATGATGGTACATA | 1,059 | 25 |
|  | Reverse | CTCCAATACTACTGTAGTTGTAAGG |  | 26 |

<Example 7> Pathogenicity Test of M2-LVP-K1 Recombinant Virus

Recombinant LVP-K1 and M2-LVP-K1 viruses recovered according to Examples 1 and 6 were inoculated in a pre-prepared Vero76 cell culture (175 T-flask, Nunc.) monolayer, and the viruses to be used for pathogenicity experiments were prepared. Before inoculation, the titers of LVP-K1 ($10^{6.7}$ TCID$_{50}$/ml) and M2-LVP-K1 ($10^{6.5}$ TCID$_{50}$/ml) viruses were measured and inoculated to be a 0.1 MOI. The number of Vero76 cells grown in full monolayer in a 175 T flask was 2 to 3×$10^{7.0}$, and 0.13 ml and 0.17 ml of each of the two flasks were diluted with 3 ml of DMEM medium and then the cells were inoculated. After virus inoculation, the medium was carefully shaken with a rocker in a CO$_2$ incubator at 37° C. and was placed in a flask, and the virus sensitization solution was washed. The sensitization solution was washed three times. Then, 50 ml of DMEM medium (containing 10% FBS) was added and cultured for 2 days. When CPE was observed, the entire culture medium was harvested by freezing and thawing at least twice in a −20° C. freezer. After harvest, the culture medium was centrifuged (4° C., 3,000 g, 10 minutes) to remove cell debris. Thereafter, the supernatant was prepared for the experiment by collecting a sample for virus titration and freezing the sample at −80° C. The virus was used for the pathogenicity test by measuring the virus titer by the TCID$_{50}$ measurement method. For the virus measurement, after dispensing Vero76 cells in a 96-well plate in 2 to 5×$10^5$ cells/ml prepared in advance, the cells were cultured for 2 to 3 days to form a monolayer, and then the cultured virus was diluted in decimal notation from the undiluted solution and 100 ul of the diluted solution thereof was inoculated and observed for 3 days again. The virus titer was measured by checking the wells in which the final CPE occurred. Virus titer was calculated according to the Reed and Muench method. The hatching eggs was determined by observing the blood vessel shape of the hatching eggs, and the allantoic fluid from the hatching eggs that had died was collected and the HA titer was immediately measured. For the HA measurement, 25 μl of pre-prepared allantoic fluid was diluted by two-fold in a U-shaped 96 well plate with an equal amount of PBS using 1% chicken red blood cells prepared in advance. Then, 25 μl of 1% chicken red blood cell solution was added to measure the HA titer and identify the egg death caused by the virus. When the hatching eggs die within 24 hours of incubation, it was considered as bacterial contamination. MDT test results are shown in Table 3.

As shown in Table 3, as a result of the evaluation, the hatching egg mortality by the M2-LVP-K1 virus undiluted solution was measured over 90 hours, and the mortality time varied from 120 hours to 170 hours. The average mortality time was 144 hours, and it was identified that the weak pathogenicity was maintained. On the other hand, the average mortality time of the LVP-K1 virus used as a control group was 140 hours, showing the same result as that of the VG/GA strain, which is known as 140 hours. Hatching egg mortality was not observed in the 10-fold and 100-fold diluted solution. Accordingly, the pathogenic change of the M2-LVP-K1 virus could not be identified through the MDT test.

TABLE 3

| Dilution rate | Undiluted solution | | | | | | | | | 1/10 | | | | | 1/100 | | | | |
|---|---|---|---|---|---|---|---|---|---|---|---|---|---|---|---|---|---|---|---|
| LVP-K1 | 144 | 170 | 144 | 120 | 120 | L | L | L | L | L | L | L | L | L | L |
| M2-LVP-K1 | 170 | 144 | 144 | 120 | 144 | L | L | L | L | L | L | L | L | L | L |

The control group was inoculated with the same amount of PBS, and it was identified that there was no hatching egg mortality.

Subsequently, in order to identify a change in the pathogenicity of the M2-LVP-K1 virus, the cerebral lesion index (ICPI, Intracerebral pathogenicity index) was measured. Table 4 shows the observed scores of the cerebral lesion index of LVP-K1 and M2-LVP-K1 recombinant viruses.

M2-LVP-K1 virus ($10^{6.3}$ TCID$_{50}$/ml, HA titer $2^6$ or higher) and LVP-K1 virus of the same titer which were a control were inoculated into the brains of 1-day-old SPF chickens. SPF 1-day-old chicks (company name) were individually reared and tested by 10 chicks each. Pathogenicity was measured while observing for 8 days by inoculating 0.05 ml into the brain of each SPF chick. In the measurement of pathogenicity, as for the main criteria for disease symptoms, the decrease in activity after virus inoculation and the phenomenon of the chicks closing their eyes and drowsing were mainly observed. Pathogenicity and mortality were measured and observed at least twice a day for 8 days. The ICPI index of M2-LVP-K1 of the present disclosure was 0.34, indicating weak pathogenicity, and the ICPI index of the LVP-K1 virus of the control group was also 0.36, identifying that the H domain mutant domain did not cause a change in pathogenicity.

TABLE 4

| Date | LVP-K1 | | | | | | | | | | M2-LVP-K1 | | | | | | | | | |
|---|---|---|---|---|---|---|---|---|---|---|---|---|---|---|---|---|---|---|---|---|
| 1 | 0 | 0 | 0 | 0 | 0 | 0 | 0 | 0 | 0 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 | 0 | 0 | 0 | 0 | 0 | 0 | 0 | 0 | 0 |
| 4 | 1 | 0 | 1 | 0 | 0 | 0 | 0 | 0 | 0 | 0 | 0 | 0 | 0 | 0 | 1 | 0 | 0 | 0 | 0 | 0 |
| 5 | 1 | 0 | 1 | 0 | 0 | 1 | 0 | 0 | 1 | 0 | 0 | 2 | 1 | 0 | 0 | 0 | 0 | 0 | 0 | 1 |
| 6 | 2 | 1 | 2 | 0 | 1 | 1 | 1 | 1 | 2 | 1 | 1 | | 2 | 1 | 1 | 0 | 2 | 0 | 0 | 2 |
| 7 | | 1 | | 1 | 2 | 2 | 1 | 1 | | 1 | 1 | | | 1 | 2 | 1 | | 2 | | 1 |
| 8 | | 1 | | 2 | | | 1 | 1 | | 1 | 2 | | | 1 | | 1 | | | 1 | |
| Total score | | | | | 29 | | | | | | | | | | 27 | | | | | |

The control group was inoculated with the same amount of PBS and it was identified that the virus of the control group was survived without lesions for 8 days.

As such, as a result of checking through MDT assay and ICPI assay, the M2-LVP-K1 virus having a mutation H domain is not a mutation capable of recovering pathogenicity, and this mutation is independent of pathogenicity. However, it may be interpreted as a result followed by increased specificity or binding ability for glycoproteins on the surface of specific cancer cells and/or expansion of the spectrum of glycoproteins that may be bound.

<Example 8> Purification of Recombinant Newcastle Disease Virus

On the previous day, Vero76 cells were cultured at $3 \times 10^5$ cells/ml, and then inoculated with the recombinant virus 0.05 MOI on the next day to obtain the highest titer of the virus supernatant after 2 days. Thereafter, the virus supernatant was centrifuged at 5,000 g at 4° C. for 10 minutes to remove floating materials, and the supernatant was collected. The collected supernatant was purified by receiving a virus fraction using size exclusion chromatography column HiScreen™ Capto™ Core 400. For the chromatography method, 25 ml of samples were loaded and 20 mM Tris-HCl (pH 7.5) buffer containing 150 mM NaCl was flowed at a flow rate of 1.6 ml/min, and absorption at 260 nm and 280 nm was measured to isolate fractions. Each fraction volume was 1.0 ml, and the fraction containing a virus was fraction nos. 2 to 10, and a total of 9.0 ml thereof was isolated. The size exclusion chromatography process was performed three times to secure the virus. For concentration of the recombinant virus, ultracentrifugation was performed at 32,000 rpm at 4° C. for 3 hours, and the supernatant was removed and resuspended in TNE buffer (10 mM Tris-HCl, 20 mM NaCl, 1 mM EDTA). The concentrated virus was subjected to ultracentrifugation at 32,000 rpm at 4° C. for 2 hours using a 10 to 50% sucrose linear gradient method. After centrifugation, the white band part of the centrifugal tube was separated to obtain a recombinant virus. Finally, the obtained recombinant virus was subjected to ultracentrifugation once more at 32,000 rpm at 4° C. for 2 hours to remove sucrose and to purify recombinant Newcastle disease viruses LVP-K1 and M2-LVP-K1.

<Example 9> Identification of Growth Kinetics of Recombinant Virus Using Vero76 Cells and HCT116 Cells M2-LVP-K1 virus was adapted to HCT116 colorectal cancer cells and Vero76 cells, and the virus was subjected for titer measurement in HCT116 cells and Vero76 cells, respectively. Vero76 cells were cultured as follows. The cells were cultured using Dulbecco's minimum essential medium (DMEM, Gibco, USA) containing penicillin-streptomycin (Gibco, USA) and 10% FBS for cell culture, and cultured using a 175 T flask. When the cells grew to form a monolayer of 70 to 80% or more, subculture was proceeded and maintained. The split ratio of Vero76 cells may be up to 1:8 and the seeding density is $1\times10^4$ cells/ml.

The culture of HCT116 cells is as follows. HCT116 cells were cultured in Roswell Park Memorial Institute 1640 Medium (RPMI1640, Gibco, USA) containing penicillin-streptomycin (Gibco, USA) and 10% FBS for cell culture, in a 37° C. incubator (5%, $CO_2$) using a 175 T flask. When the cells grew to form a 70 to 80% monolayer in the flask, the cells were maintained through subculture from 1:4 to 1:6. Seeding density was about 2 to $4\times10^4$ cells/ml.

In order to conduct a comparative experiment on the proliferation of LVP-K1 virus and M2-LVP-K1 virus using the prepared Vero76 cells and HCT116 cells, the culture medium of Vero76 cells and HCT116 cells that form a monolayer of 70 to 80% or more in a 75 T flask was removed. Thereafter, 10 ml of serum-free DMEM medium was put into the flask and carefully shaken to wash the cells. After repeating this process 2 or 3 times, LVP-KI virus and M2-LVP-KI virus (0.1 MOI) were put into the flask and were shaken in a 37° C. incubator at intervals of 10 minutes, and the virus was sensitized for 1 hour. After removing the virus solution, 10 ml of serum-free DMEM medium was put into the flask to remove the remaining virus solution. Then, 20 ml of DMEM medium to which 5% FBS was added was put thereinto, and the virus was collected at 48 hours to measure the virus titer by the $TCID_{50}$ measurement method.

For the general $TCID_{50}$ measurement method, Vero76 cells were used. However, in this study, it was also identified in HCT116 cells to compare specific binding to colorectal cancer cells as well as Vero76 cells. LVP-K1 cultured in Vero76 cells was used as a positive control group, and a higher titer was identified in Vero76 cells of which were $10^{4.7}$ $TCID_{50}$/ml in Vero76 cells and $10^{3.7}$ $TCID_{50}$/ml in HCT116 cells. M2-LVP-K1 virus cultured in Vero76 cells showed a higher titer in HCT116 cells of which were $10^{3.7}$ $TCID_{50}$/ml in Vero76 cells and $10^{4.1}$ $TCID_{50}$/ml in HCT116 cells. M2-LVP-K1 virus cultured in HCT116 cells showed a higher titer in HCT116 cells of which were $10^{4.9}$ $TCID_{50}$/ml in Vero76 cells and $10^{5.5}$ $TCID_{50}$/ml in HCT116 cells. In particular, the highest titer was identified when the titer of M2-LVP-K1 virus cultured in HCT116 cells was measured using HCT116 cells (FIG. 7). This result may support the basis that the M2-LVP-K1 virus has a higher binding ability to colorectal cancer cells.

\<Example 10\> Specific Apoptosis in Colorectal Cancer Cells Compared to Various Cancer Cells of LVP-K1 and M2-LVP-K1 Viruses In order to identify the apoptosis effect of cancer cells caused by LVP-K1 and M2-LVP-K1 virus infection, the cytopathic effect (CPE) was identified and MTT assay experiment was performed. As cells for cytopathic effect (CPE) identification, colorectal cancer (HCT116), normal colorectal cells (CCD-18Co), lung cancer (A549), and glioblastoma (T98G) were used. As cells for the MTT assay, colorectal cancer (HCT116), lung cancer (A549), and glioblastoma (T98G) were used.

In order to identify the cytopathic effect (CPE) of the virus, microscopic observations were made at 3, 6, 9, and 12 hours after sensitization of LVP-K1 and M2-LVP-K1 viruses with 0.1 MOI using cells cultured on the previous day according to a general cell culture method. The cells in which CPE was identified at the fastest rate were HCT116 colorectal cancer cells sensitized with M2-LVP-K1 virus and were identified at 6 hours. On the other hand, LVP-K1 virus did not show CPE until 12 hours.

MTT assay was performed according to a conventional method and describes the detailed experimental procedure. Roswell Park Memorial Institute 1640 Medium (RPMI1640, Gibco, USA) containing penicillin, streptomycin (Gibco, USA) and 10% FBS for cell culture of $1 \times 10^4$ HCT116 cells per well in a 96-well plate for 24 hours was used and cultured in a 37° C. incubator (5% $CO_2$), and LVP-K1 virus and M2-LVP-K virus were infected to be made at 0.1, 1, and 10 MOIs. For the reliability of the results, 4 wells of the same condition were prepared to proceed. After infection, the cells were cultured in a 37° C. incubator (5% $CO_2$), and 72 hours after infection, 20 μl of MTT solution (CellTiter 96© AQueous One solution Cell Proliferation Assay, Bio-Rad, USA) was added to each well and the cells were cultured for 1 hour in an incubator (5% $CO_2$). Cell death was measured by measuring the absorbance of light having a wavelength of 450 nm using an iMark Microplate Reader (Bio-Rad, USA). Thereafter, the relative death rate (%) to the negative control group was identified. The results are shown in FIGS. 8A-8E.

Figure 8A:
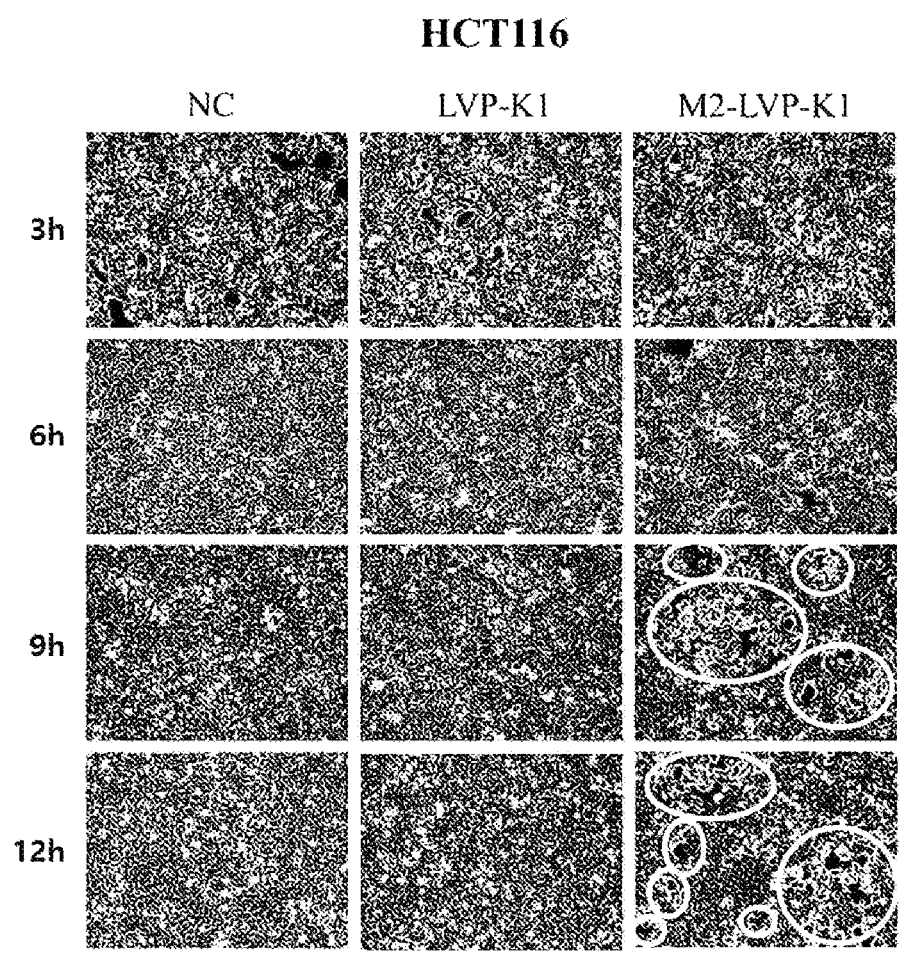
FIGS. 8A-8E are views showing the cytopathic effect (CPE) in various cancer cells and colorectal normal cells infected with the M2-LVP-K1 virus of the present disclosure and the relative death rate (%) to the negative control group.
Figure 8B:
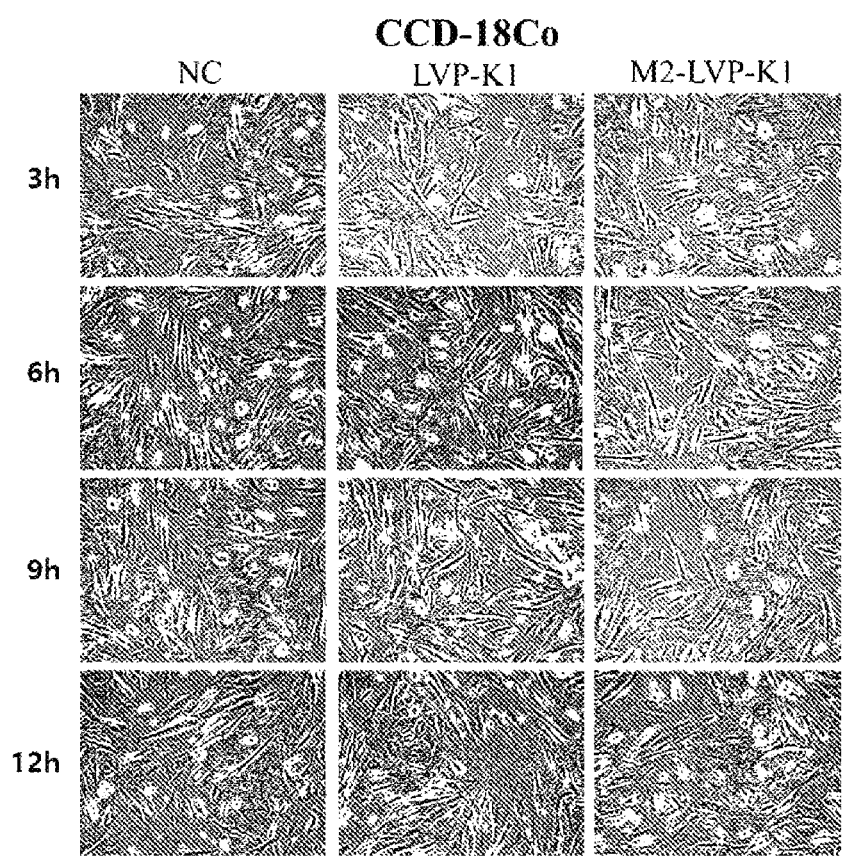
Figure 8C:
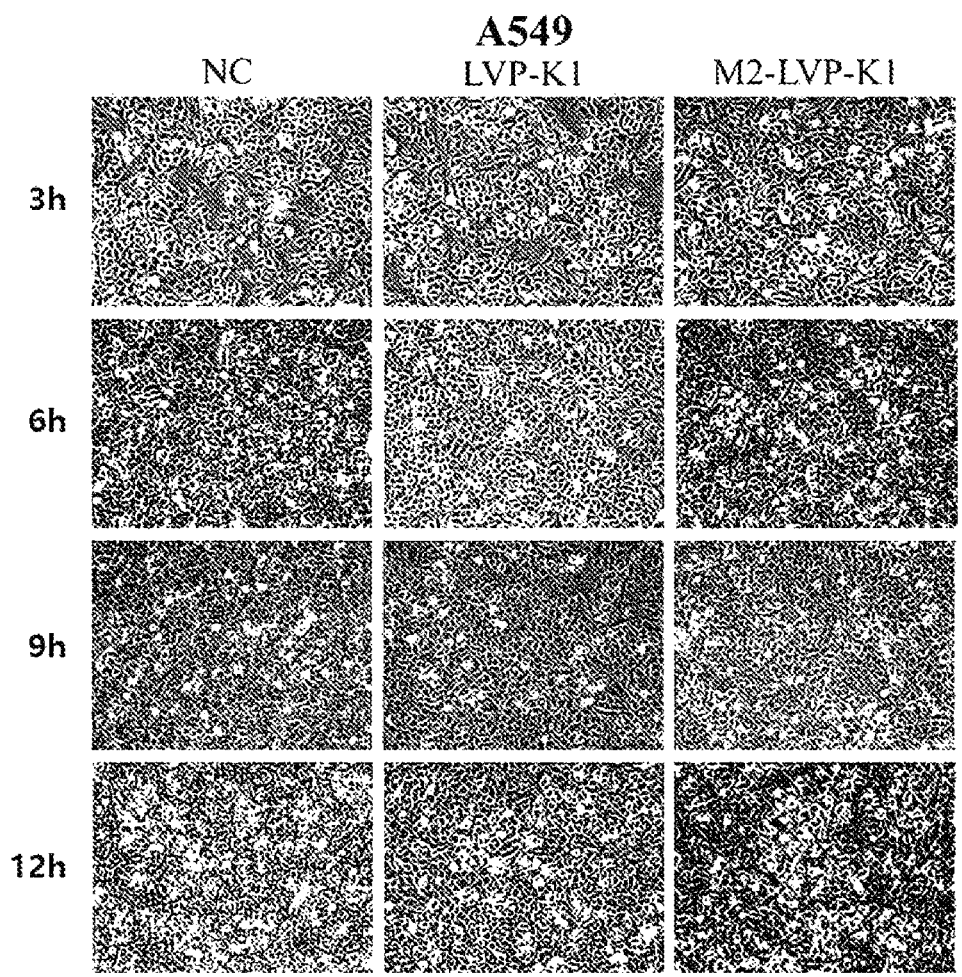
Figure 8D:
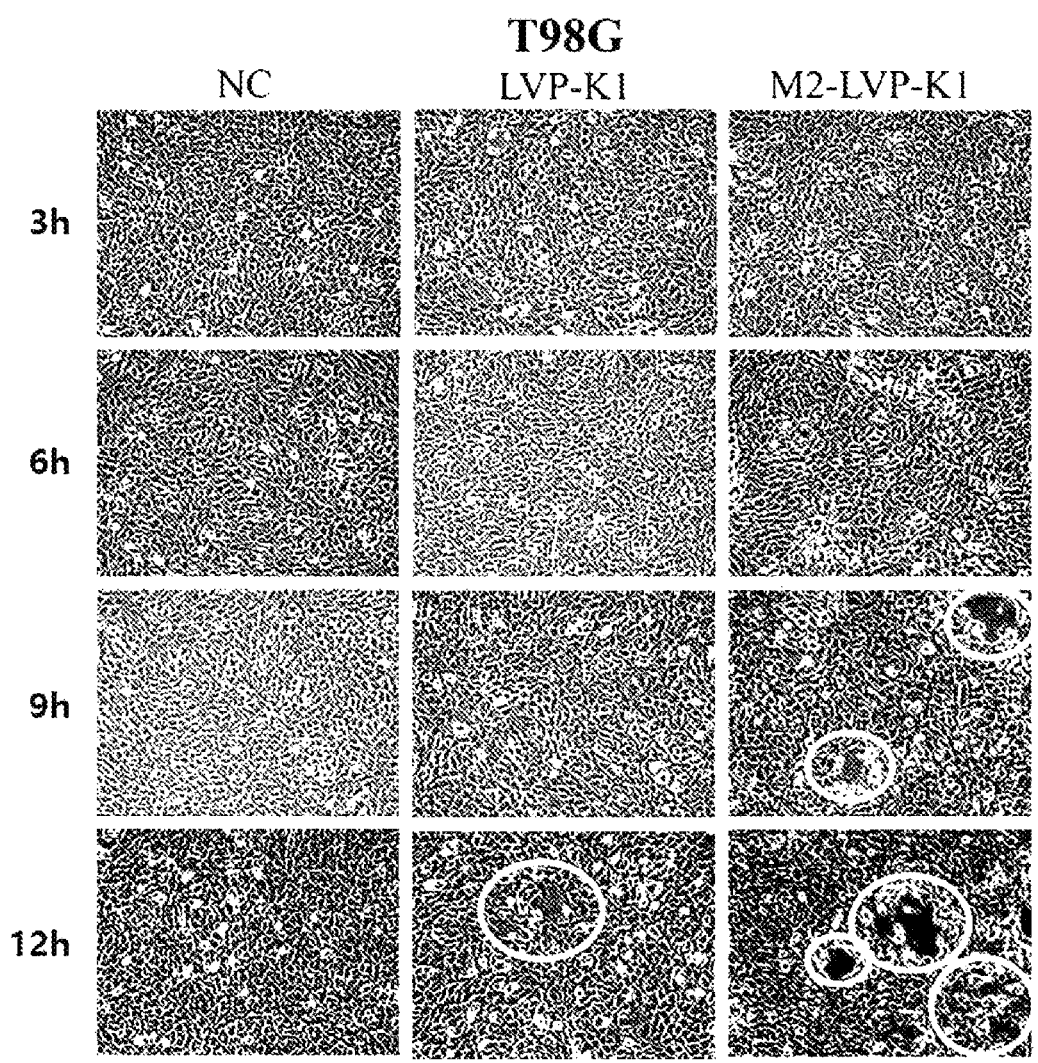
Figure 8E:
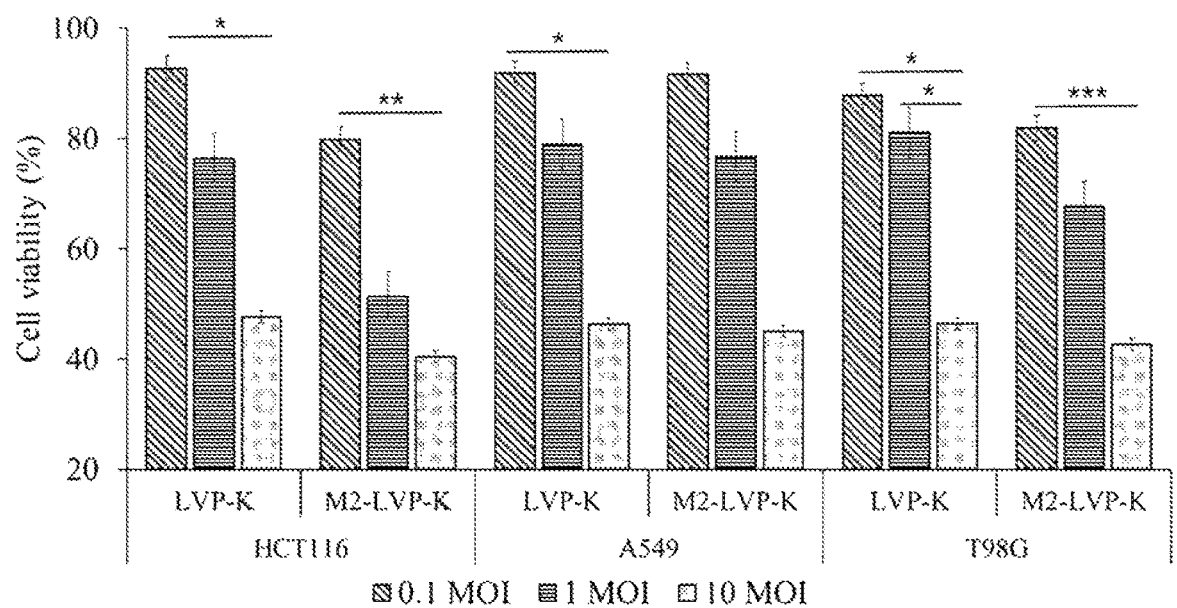

FIGS. 8A to 8D show the results of observing the cytopathic effect (CPE) in various cancer cells (T98G; glioblastoma, A549; lung cancer) including M2-LVP-K1 infected colorectal cancer cells (HCT116) and colorectal normal cells (CCD-18Co) of the present disclosure through a microscope. FIG. 8E shows the result of identifying the relative death rate (%) of the negative control group on the 4th day after infection so that the virus is made at 0.1, 1, and 10 MOI in colorectal cancer cells (HCT116) and various cancer cells (T98G; glioblastoma, A549; lung cancer). * indicates P value 0.05 or less,  indicates P value 0.01 or less, and * indicates P value 0.001 or less.

As shown in FIGS. 8A-8E, the virus into which the M2-LVP-K1 gene was inserted showed a faster cancer cell killing effect than the LVP-K1 virus. This killing effect on HCT116 colorectal cancer cells may be identified more clearly in the M2-LVP-K1 virus.

In particular, as shown in FIG. 8E, the difference in the cancer cell killing effect shows a difference as the concentration of the virus inoculated into the cells is lower. The recombinant NDV virus, LVP-K1 virus, also originally has an oncolytic effect, so it does not show a difference at high concentrations. However, it is considered that the M2-LVP-K1 virus, which has increased binding ability to sialic acid or glycoprotein expressed on HCT 116 cell surface at 1 MOI or less, increased the apoptosis effect of cancer cells and affected apoptosis.

\<Example 11\> Identification of Cancer Cell Proliferation Inhibitory Effect Upon Intratumoral Inoculation of Virus Using Colorectal Cancer Xenograft Nude Mice The cancer tissue growth inhibitory effect of LVP-K1 and M2-LVP-K1 viruses was measured using a xenograft model. $1 \times 10^7$ cells/ml of cultured HCT116 cells were dissolved in RPMI medium, 100 μl thereof was mixed with an equal amount of Matrigel (Corning) and inoculated into the left hip of the mouse to establish the HCT116 xenograft model. For the mice used, 12 SPF female BALB/c nude mice weighing about 14 to 19 g were purchased from SLC (Japan) and randomly divided into 4 mice per group for experiments. Each experimental group was divided into a group in which LVP-K1 virus, M2-LVP-K1 virus and PBS were directly injected into cancer tissues. The concentration of the inoculated virus was $10^8$ $TCID_{50}$/ml, and the tumor growth rate was compared between the treatment group and the control group by inoculating 100 μl each. Virus inoculation was performed three times at 3-day intervals from when the cancer tissue size reached an average of 100 to 200 mm3 on the 5th day after HCT116 cell inoculation. For 14 days after virus inoculation, changes in cancer tissues were observed every day, and the last change in cancer tissues was observed on day 27 after virus inoculation. The size of the cancer tissues was calculated using the formula ½×(smallest diameter)²×(largest diameter).

Figure 9A:
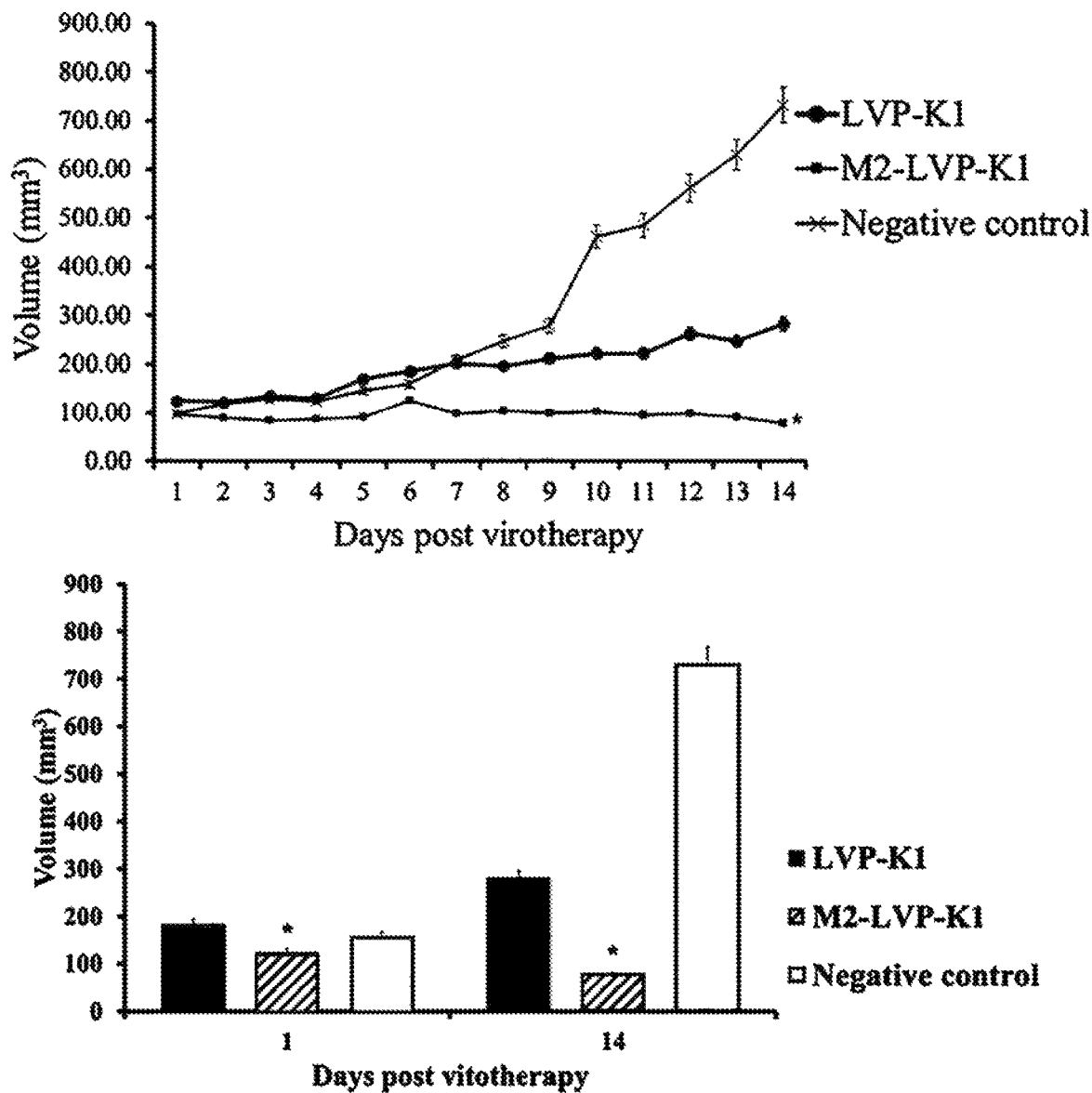
FIGS. 9A-9C are diagrams showing tumor growth inhibition in a colorectal cancer xenograft mouse model.
Figure 9B:
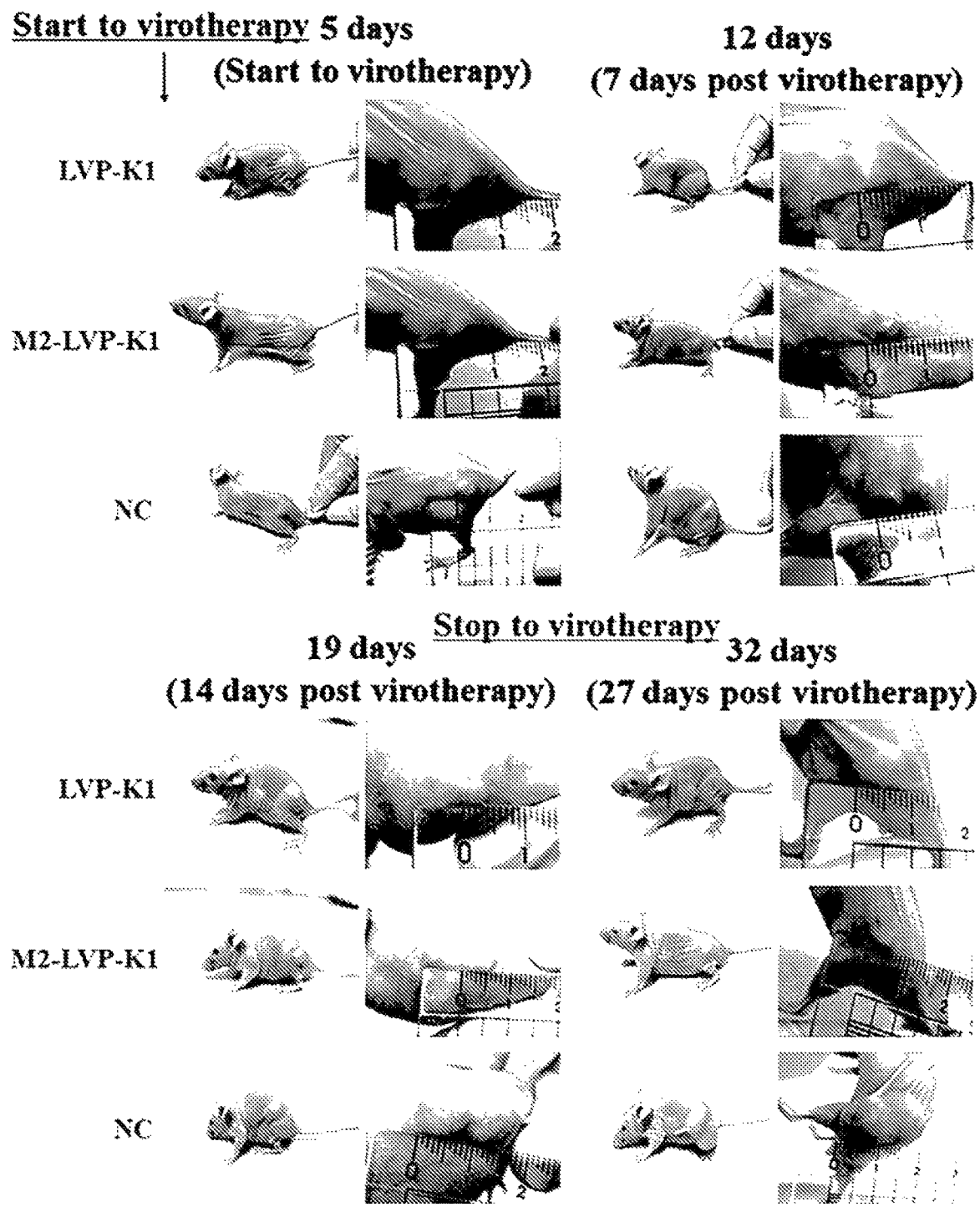
Figure 9C:
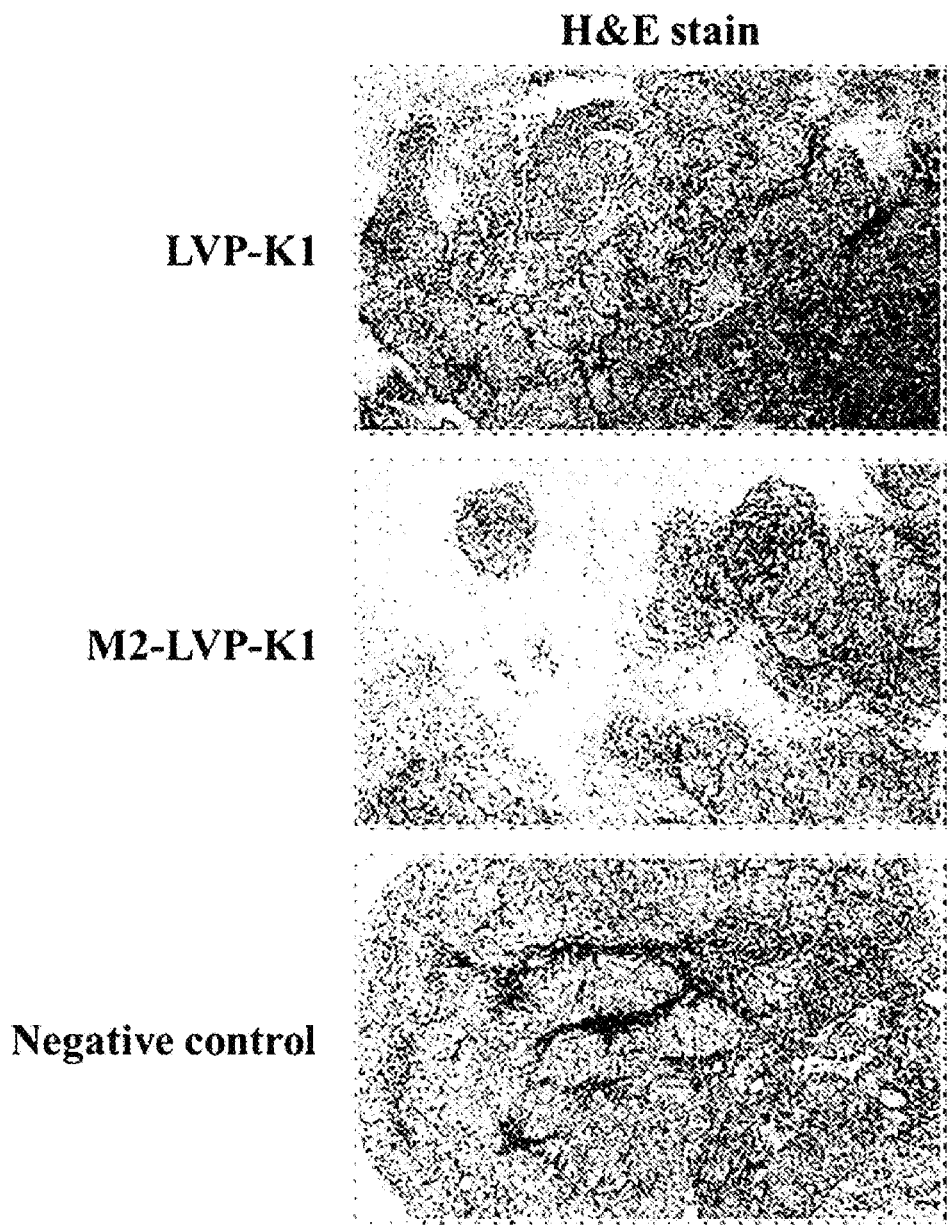

Through FIGS. 9A, 9B and 9C, the virus-treated group was 200 mm³ or less, and a difference of about 10-fold from the control group 2,000 mm³ was identified, identifying that the tumor was remitted. In addition, it was identified that the LVP-K1 virus had a lower oncolytic effect than the M2-LVP-K1 virus. These results suggest that the improvement of the colorectal cancer cell-specific binding ability of the M2-LVP-K1 virus had an effect on apoptosis.

It was observed that the cancer tissue was reduced most quickly and effectively in the M2-LVP-K1 virus inoculation group. In addition, as shown in FIG. 9C, in the pathological tissue pattern, a high level of lymphocyte infiltration was observed in the M2-LVP-K1 group, and a low level of tumor cells was observed. In the case of the LVP-K1 group, a moderate level of lymphocyte infiltration was observed, and the cell density was rather high, which was different from that of the M2-LVP-K1 virus. Based on these findings, the cancer cell killing effect of the M2-LVP-K1 group is considered to be very high, and the LVP-K1 group does not appear to have a higher cancer cell killing effect than the M2-LVP-K1 virus.

A new oncolytic virus for treating colorectal cancer was constructed using the NDV virus that does not cause an immune response in mammals and does not generate antibodies, and the effect of inhibiting cancer cell proliferation on colorectal cancer was identified. There are many NDV viruses that disappear from normal cells without reaching cancer cells due to innate immunity immediately after infection. In addition, due to the dilution effect of intravenous injection, rather than a simple recombinant virus that has been used already, it is a very important task to develop a recombinant NDV virus that is expressed as a protein in cancer cells to increase efficacy by inserting various genes for cancer cell proliferation inhibitory effect, apoptosis induction, and immune response induction. Further research will be needed in the future for further development. The present disclosure demonstrates that the NDV virus has an oncolytic function in colorectal cancer cells to some extent, and that the NDV recombinant virus with increased binding ability to colorectal cancer is constructed and the effect thereof is improved.

Hereinbefore, although specific embodiments of the present disclosure have been described in detail, those skilled in the art who understand the spirit of the present disclosure may easily suggest other embodiments included in other retrogressive embodiments or the scope of the spirit of the present disclosure by adding, modifying, or deleting other components within the scope of the same spirit. Therefore, the disclosed embodiments should be considered in an illustrative in all aspects rather than a restrictive perspective. The scope of the present disclosure is defined by the following claims rather than by the preceding description. It should be interpreted that all changes or modifications derived from the meaning and scope of the claims and their equivalents are included in the scope of the present disclosure.

ACCESSION NO.

Depository Institution: Korean Collection for Type Cultures (KCTC) of Korea Research Institute of Biotechnology and Bioscience
Accession No.: KCTC14630BP
Deposit Date: 2021 Jun. 30.

The invention claimed is:

1. A recombinant vector for constructing a colorectal cancer-targeted oncolytic virus, wherein the recombinant vector has the sequence of SEQ ID NO: 1.

2. The recombinant vector of claim 1, wherein the recombinant vector further includes a transgene cassette consisting of an IGS sequence (gene end (GE), intergenic sequence (IG), and gene start (GS)) and a multiple cloning site (MCS).

3. An oncolytic virus for treating colorectal cancer comprising the recombinant vector for constructing the colorectal cancer-targeted oncolytic virus according to claim 1, wherein the oncolytic virus is a recombinant Newcastle disease virus having accession No. KCTC14630BP.

4. A pharmaceutical composition for treating colorectal cancer comprising the recombinant Newcastle disease virus of claim 3 as an active ingredient and a pharmaceutically acceptable carrier.

5. A method for treating colorectal cancer, the method comprising administering the composition of claim 4 to a subject in need thereof.

6. A method for treating colorectal cancer, the method comprising administering the oncolytic virus of claim 3 to a subject in need thereof.

* * * * *

SEQUENCE LISTING

```
<160> NUMBER OF SEQ ID NOS: 26

<210> SEQ ID NO 1
<211> LENGTH: 19054
<212> TYPE: DNA
<213> ORGANISM: Artificial Sequence
<220> FEATURE:
<223> OTHER INFORMATION: M2-LVP-K1

<400> SEQUENCE: 1
accaaacaga gaatccgtaa ggtacgatag aaggcgaagg agcaatcgaa gtcgtacggg      60
tagaaggtgt gaatctcgag tgcgagcccg aagctcaaac tcgagagagc cttctgccaa     120
aatgtcttct gtattcgatg agtacgagca gctcctcgcg gctcagactc gccccaatgg     180
agctcatggc ggaggagaga aggggagcac cttaaaggta gaagtcccgg tattcactct     240
caacagtgat gacccagaag atagatggaa cttgtcagtg ttttgtcttc ggattgctgt     300
tagcgaggat gccaacaaac cacttaggca aggtgctctc atatctctct tatgttccca     360
ctctcaagtg atgaggaacc atgttgccct tgcggggaaa cagaatgagg ccacactggc     420
tgttcttgag atcgatggtt ttaccaacgg cgtgccccag ttcaacaaca ggagtggagt     480
gtctgaagag agagcacaga gatttatgat gatagcaggg tctctccctc gggcatgcag     540
caacggtacc ccgttcgtca cagctggggt tgaagatgat gcaccagaag acattactga     600
taccctggag aggatcctct ctatccaggc tcaagtatgg gtcacggtgg caaaggccat     660
gactgcatat gagacagcag atgagtcaga aacaagaaga atcaataagt acatgcagca     720
aggcagggtc cagaagaagt acatcctcca ccccgtatgc aggagcgcaa tccaactcac     780
aatcagacag tctctggcgg tccgcatctt tttggttagc gagcttaaga gaggccgcaa     840
cacggcaggt gggacctcca cctattacaa cttggtgggg gatgtagact catacatcag     900
gaacactggg ctaactgcat tcttcctgac acttaaatat ggaattaaca ccaagacatc     960
agcccttgca cttagcagcc tctcaggcga tatccagaaa atgaagcagc tcatgcgctt    1020
gtatcggatg aaaggagata atgcgccgta catgacattg ctcggtgaca gtgaccagat    1080
gagctttgca cctgccgagt atgcacaact ttactccttt gccatgggta tggcatcagt    1140
cctagataaa ggaactagca ataccaatt tgccagggac tttatgagca catcattctg    1200
gagacttgga gtagagtacg ctcaggctca aggaagtagc atcaatgagg atatggccgc    1260
cgagctaaag ctaaccccag cagcaaggag aggcctggca gctgctgccc aaagagtgtc    1320
tgaggagacc agcagcatgg acatgcccac ccaacaagcc ggggtcctca ctggactcag    1380
cgacggaggc tcccaagccc cccaaggtgc actgaacaga tcacaagggc aaccggacac    1440
```

```
cggggatggg gagacccaat ttctggatct gatgagagcg gtggcaaata gcatgagaga   1500
agcgccaaac tctgcgcagg gcacccctca accggggcct cccccaaccc ctgggccctc   1560
tcaagacaat gacaccgact gggggtactg accgacagca cccagtttgc ttctatgagg   1620
tcatcccaat tcctctgccc acaccccacc cctcaatccg caatcccgca tggccaaacc   1680
cacaaacgaa ccccccctgtc tccctcctct cccccagccc cacaacccca cctgcccagg   1740
gcaacatagg tacaatgcga cccactaata atcaatacag ggccaaagaa attagaaaaa   1800
agtacgggta gaagggagac attcagagat cagggcgagt cacccgggtc tctgctctcc   1860
cttctaccta gtggattagg atggagatgg ccacctttac agatgcggag atcgacgagc   1920
tatttgagac cagtggaact gtcattgaca gcataattac ggcccaggga aaaccagtag   1980
agactgttgg aaggagtgca atcccacaag gcaaaactaa ggctttgagc gcagcatggg   2040
agaagcatgg gagcatccag tcaccagcca gccaagacac ccctgatcga caggacagat   2100
cagataaaca actgtccaca cccgagcaag cgagtccaaa cgacagcccc ccagccacat   2160
ccactgacca gcctcccact caggctgcag atgaggccgg cgatacacag ctcaagaccg   2220
gagcaagcaa ctctctgctg tcgatgcttg ataaactcag caataagtca tctaatgcta   2280
aaaagggccc agggtcgagc cctcaagaaa ggcatcatca acgtctgact caacaacagg   2340
ggagtcaaca aagccgcgga aacagccaag agagaccgca gaaccaggcc aaggccatcc   2400
ctggaaacca ggtcacagac gcgaacacag catatcatgg acaatgggag gagtcacaac   2460
tatcagctgg tgcaacccat catgctctcc gatcagagca gagccaagac aatactcctg   2520
cacctgtgga tcatgtccag ctacctgtcg actttgtgca ggcgatgatg tctatgatgg   2580
aggcgatatc acagagggta agtaaagttg actatcagct ggaccttgtc ttgaaacaga   2640
catcttctat ccccatgatg cggtctgaaa tccagcagct gaaaacgtct gttgcggtca   2700
tggaagccaa tttgggcatg atgaagatcc tggaccctgg ttgtgccaac gtttcatctc   2760
taagtgatct acgggcagtt gcccgatccc acccggtttt aatttctggc cccggagacc   2820
catctcctta tgtgacccaa gggggcgaaa tggcactcaa taaactttcg caaccggtgc   2880
aacacccctc tgaattgatt aaacccgcca cggcaagcgg gcctgatata ggagtggaga   2940
aagacactgt ccgtgcattg atcatgtcac gccctatgca tccgagctct tcagctaggc   3000
tcttgagcaa actggacgca gccggatcga ttgaggaaat cagaaaaatc aagcgccttg   3060
cactgaatgg ctaatcacca ccgcaacccg cagcagatcc ctgtccaccc agcaccacac   3120
ggtatctgca ccaagctcct ctctgcaaac ccaaggtcca acaccccgag cgacaaccct   3180
gtcctgcttc ctctgcccca ctaaatgatc gcgcagctgc aatcaattca gctatattaa   3240
ggattaagaa aaaatacggg tagaatcgga gtgccccgat tgtgccaaga tggactcatc   3300
taggacaatc gggctgtact ttgattctac ccttccttct agcaacctgc tagcattccc   3360
gatagtccta caagacacag gggacgggaa gaagcaaatc gccccgcaat acaggatcca   3420
gcgtcttgac tcgtggacag acagcaaaga agactcggta ttcatcacca cctatggatt   3480
catctttcag gttgggaatg aagaagccac tgtcggcatg atcaatgata atcccaagcg   3540
cgagttactt tccactgcca tgctatgcct agggagtgta ccaaatgtcg gagatcttgt   3600
tgagctggca agggcctgcc tcactatggt ggtaacatgc aagaagagtg caactaacac   3660
cgagagaatg gtcttctcag tagtgcaggc accccaggtg ctgcaaagct gtagggttgt   3720
ggcaaacaaa tactcgtcgg tgaatgcagt caagcacgtg aaagcaccag agaagattcc   3780
tgggagcgga accctagagt acaaagtgaa ctttgtctct ctgaccgtgg tgccaagaaa   3840
```

```
ggacgtctac aagataccaa ctgcagcact taaggtctct ggctcaagtc tgtacaatct    3900
tgcgctcaat gtcactattg atgtggaggt agacccgaag agcccgttgg tcaaatccct    3960
ttccaagtcc gacagtgggt actatgctaa tctcttctta catattgggc ttatgtccac    4020
tgtagataag aaggggaaga aagtgacatt tgacaagctg gaaaggaaga taaggagact    4080
tgatctatct gtagggctta gtgacgtgct cggaccttcc gtgcttgtaa aggcgagagg    4140
tgcacggact aagctgctgg cacctttctt ctctagcagt gggacagcct gctatcccat    4200
agcaaatgcc tctcctcagg tggccaagat actctggagc caaaccgcgt acctgcggag    4260
tgtaaaagtc attatccaag cgggcaccca gcgtgctgtc gcagtgaccg ccgaccacga    4320
ggttacctct actaagctgg agaaggggca taccattgcc aaatacaatc ccttcaagaa    4380
ataggctgca tctctgagat tgcactccgc ccatcttccc ggatcaccat gacactaaat    4440
aatgatctgt cttgattact tatagttagt tcgcctgtct atcaaattag aaaaaacacg    4500
ggtagaagat tctggatccc ggttggcgcc ttcaaggtgc aagatgggct ccagatcttc    4560
taccaggatc ccagtaccct ttatgctgac cgtccgagtc atgttggcac tgagttgcgt    4620
ctgtccgacc agcgcccttg atggcaggcc tcttgcagct gcagggattg tggtaacagg    4680
agacaaagca gtcaacatat acacctcatc tcagacaggg tcaatcataa tcaagttact    4740
cccaaatatg cccaaggata aagaggcgtg tgcaaaagcc ccgttggagg catacaacag    4800
gacattgact actttgctca ccccccttgg tgattctatc cgtaggatac aagagtctgt    4860
gaccacgtcc ggaggaggga gacaggggcg cctataggc gccattatcg gtggtgtagc    4920
tctcggggtt gcaaccgctg cacagataac agcagcctcg gctctgatac aagccaatca    4980
aaatgctgcc aacatactcc ggctaaaaga gagcattgct gcaaccaatg aggctgtgca    5040
cgaggtcact aatggattat cacaactagc agtggcagtt gggaagatgc agcaatttgt    5100
taatgaccag tttaataaaa cagctcagga attggactgt ataaaaatta cacagcaggt    5160
tggtgtagaa ctcaacctgt acctaactga attgactaca gtattcgggc cacaaatcac    5220
ttcccctgcc ttaactcagc tgactatcca ggcgctttac aatctagctg gtgggaatat    5280
ggattacttg ttgactaagt taggtgtggg gaacaaccaa ctcagctcat taattagtag    5340
tggcctgatc accggcaacc ctattctgta cgactcacag actcaactct gggtataca    5400 ggtaacccta ccctcagtcg ggaacctaaa taatatgcgt gccacctacc tggaaaacctt    5460 gtctgtaagt acaaccaaag gatttgcctc agcacttgtc ccaaaagtag tgacacaggt    5520
cggttccgtg atagaagagc ttgacacctc gtactgtata gagaccgatt tggatctata    5580
ttgtacaaga atagtgacat tccctatgtc tcctggtatt tattcctgtt tgagtggcaa    5640
tacatctgct tgcatgtact caaagactga aggcgcactc actacgccgt atatgaccct    5700
caaaggctca gttattgcta actgtaagat gacaacatgt agatgtgcag accccccggg    5760
tatcatatcg caaaattatg gagaagctgt gtctctaata gataggcaat catgcaatat    5820
cttatcctta gacgggataa cttttgaggct cagtgggaa tttgatgcaa cttatcaaaa    5880
gaatatctca atacaagatt ctcaagtaat agtgacaggc aatcttgata tctcgactga    5940
gcttgggaat gtcaacaact cgataagtaa tgctttggat aagttagagg aaagcaacag    6000
caaactagat aaggtcaatg tcaaactgac cagcacatcc gctcttatta cctatatcgt    6060
tttaactgtc atatctcttg tatgtggtat acttagcctg gttctagcat gctacctgat    6120
gtacaagcaa aaggcgcaac agaagacctt gttgtggctt gggaataata ccctagacca    6180
```

```
gatgagggcc actacaaaaa tgtgaatgcg gatgagaggc agaaacatcc ccaatagcag    6240
tttgtgtgta aagtctgaca gcctgttaat tagaagaatt aagaaaaaac taccggatgt    6300
agatgaccaa agggcgatat acgggtagaa cggtcgggga ggccgtccct caatcgggag    6360
ccgggcctca caacatccgt tctaccgcat caccaatagc agttttcagt catggaccgc    6420
gcagttagcc aagttgcgct agagaatgat gaaagagagg caaagaatac atggcgcttg    6480
gtattccgga tcgcaatcct actctcaacg gtggtgacct tagccatctc tgcagccgcc    6540
cttgcatata gcatggaggc cagcacacct agcgatcttg taggcatacc gactgcgatc    6600
tctagagcag aggaaaagat tacatctgca ctcggttcca atcaagatgt agtagatagg    6660
atatataagc aggtggccct cgaatctcca ctggcattgc taaacaccga atctacaatt    6720
atgaacgcaa taacgtctct ctcttatcga atcaatgggg ccgcaaatag cagcggatgt    6780
ggagcaccca ttcatgatcc agattatatt ggaggaatag gtaaagaact tattgtagat    6840
gatgctagcg acgtcacatc atactatccc tctgcgttcc aagaacacct gaactttatc    6900
ccggcgccta ctacaggatc aggttgcact cggatacccct catttgacat gagcgctacc    6960
cactactgtt atactcacaa tgtgatatta tctggctgca gagatcactc gcactcacat    7020
caatatttag cacttggtgt gcttcggaca tctgcaacag ggagggtatt cttttccact    7080
ctgcgttcca tcaatctgga tgacacccaa aatcggaagt cttgcagtgt gagtgcaacc    7140
cccttgggtt gtgatatgct gtgctctaaa gtcacagaga ctgaagaaga ggattataac    7200
tcagctatcc ccacgtcgat ggtacatgga aggttagggt tcgacggcca ataccacgag    7260
aaggacctag atgtcacaac actattcgag gactgggtgg caaactaccc aggagtaggg    7320
ggcgggtctt ttattgacaa ccgcgtatgg ttcccagttt acggagggct aaaacccaat    7380
tcgcccagtg acaccgcaca agaagggaaa tatgtaatat acaagcgata caatgacaca    7440
tgtccagatg agcaagatta tcagattcaa atggctaagt cttcatataa gcctgggcgg    7500
tttggaggga aacgcgtaca gcaggccatc ttatctatca aagtgtcaac atccttgggc    7560
gaggacccgg tactgactgt accgcccaac acagtaacac tcatgggggc cgaaggcaga    7620
gttctcacag tagggacatc tcatttcctt tatcagcgag ggtcatcata cttctcccct    7680
gccctactat atcctatgat agtcagcaac aaaacagcca ctcttcatag tccttataca    7740
ttcaatgcct tcactcgacc aggtagtgtc ccttgccagg cttcagcaag atgccctaac    7800
tcatgtgtta ccggagtcta tactgatcca tatcccttgg tcttctatag gaaccacacc    7860
ttgcgagggg tattcgggac gatgcttgat gataaacaag caagactcaa ccctgtatct    7920
gcagtatttg acagcatatc ccgcagtcgc ataacccggg tgagtggaag cagcaccaag    7980
gcagcataca caacatcaac atgttttaaa gttgtaaaga ccaataaaac ctattgtctc    8040
agcattgccg aaatatccaa taccctcttc ggggaattca gaatcgtccc tttactagtt    8100
gagattctca aggatgatgg ggttagagaa gccaggtcta gccggttgag tcaactgcga    8160
gagggttgga aagatgacat tgtatcacct atcttttgcg acgccaagaa tcaaactgaa    8220
taccggcgcg agctcgagtc ctacgctgcc agttggccat aatcagctag tgctaatgtg    8280
attagattaa gtcttgtcgg tagtcacttg attaagaaaa aatgtgggtg gtagcgggat    8340
ataaggcaaa acaactcaag gaggatagca cgggtaggac atggcgagct ccggtcccga    8400
gagggcggag catcagatta tcctaccaga gtcacacctg tcttcaccat tagtcaagca    8460
caaactactc tattactgga aattaactgg gctaccactc cctgacgagt gtgacttcga    8520
ccacctcatt ctcagccgac aatggaagaa aatacttgaa tcggcctccc ctgacactga    8580
```

```
gagaatgata aaacttggaa gggcagtgca ccagactctc aaccacaatt ccaagataac   8640
cggagtactc catcccaggt gtttagaaga attggctagt attgaggttc ctgactcaac   8700
caacaagttt cggaagatcg agaagaaaat ccaaattcac aacacaaggt atggagaact   8760
gttcacaaga ctgtgcacgc atgtagagaa gaaattgttg ggatcatctt ggtctaataa   8820
tgtcccccgg tcagaagagt tcaacagcat ccgtacagat ccggcattct ggtttcactc   8880
aaaatggtcc acaactaagt ttgcatggct ccatataaaa cagattcaaa ggcatctgat   8940
tgtggcagca agaacaaggt ccgcagccaa caaattggtg acgctgaccc ataaggtagg   9000
ccaagtcttt gttactcctg agcttgtcat tgtgacacat acagatgaga acaagttcac   9060
gtgtcttacc caggaacttg tgttgatgta tgcagatatg atggagggca gagatatggt   9120
caacataata tcatccacgg cggcacatct caggagccta tcagagaaaa ttgatgacat   9180
tctgcggtta gtagatgccc tggcaaaaga tctgggtaat caagtctacg atgttgtagc   9240
actcatggag ggatttgcat acggcgccgt ccagctgctt gagccgtcag gtacattcgc   9300
aggggatttc ttcgcattca acctgcagga gctcaaagac actttgatcg gcctccttcc   9360
taaggatata gcagaatctg tgactcacgc aatagccact gtattctctg cttagaaca   9420 aaatcaagcg gctgagatgc tgtgcctgtt gcgtctatgg ggccacccat tacttgagtc   9480
ccgtattgcg gcaaaagcag taaggagcca aatgtgcgca ccaaaaatgg tagactttga   9540
tatgatcctc caggtattgt ctttctttaa aggaacaatc atcaacggat acagaaagaa   9600
gaatgcaggt gtttggccac gtgtcaaagt agatacgata tacgggaagg tcattgggca   9660
gctacacgct gattcagcgg agatttcaca cgatatcatg ttgagagagt acaagagttt   9720
atctgcgctt gaattcgagc catgtataga atacgaccct atcaccaatc tgagcatgtt   9780
tctaaaagac aaggcgatcg cacacccgaa agacaactgg ctcgccgcgt ttaggcgaaa   9840
ccttctctct gaggaccaga agaaacatgt aaaggaggca acctctacta accgtctctt   9900
gatagagttc ttagagtcaa atgattttga tccatataag gagatggaat atctgacgac   9960
ccttgagtac ctaagagatg acaatgtggc agtatcatac tcgctcaagg agaaggaagt  10020
gaaggttaat gggcggattt tgctaagct aacaaagaaa ttaaggaact gtcaagtgat  10080
ggcggaaggg atcttagctg accagattgc acctttcttt caagggaatg ggtcattca  10140 ggatagcata tctttaacca agagtatgct agcgatgagt caattgtctt caacagcaa  10200 taagaaacgt atcactgact gcaaagaaag agtagcctca aaccgcaatc acgatcaaaa  10260
gagcaagaat cgtcggagag ttgccacttt tataacgact gacctgcaaa agtactgtct  10320
taattggaga tatcagacaa tcaaactgtt cgctcatgcc atcaatcagc tgatgggctt  10380
acctcacttc ttcgaatgga ttcatctaag actaatggat actacgatgt tgtaggaga  10440 ccctttcaat ccccaagtg acccaactga ctgtgatctc tcaagagtcc caaatgatga  10500
catatatatt gtcagtgcta gaggggtat tgagggatta tgtcagaagc tatggacaat  10560
gatctcaatt gctgcaatcc aacttgctgc agcaagatca cattgtcgcg tcgcctgtat  10620
ggtacagggt gacaatcaag taatagctgt aacgagagag gtaaggtcag atgactcccc  10680
ggaaatggtg ttaacacaat tgcatcaagc cagtgataat ttcttcaagg aattgattca  10740
tgttaatcat ttgattggcc ataatttgaa ggatcgtgaa acaatcagat cagacacatt  10800
cttcatatac agcaaacgaa tattcaaaga tggagcaata ctcagtcaag tcctcaaaaa  10860
ttcatctaaa ttagtgctaa tatcaggcga ccttagtgaa aacaccgtaa tgtcctgtgc  10920
```

```
caacattgca tctactatag cacggctgtg cgagaacggg cttccaaagg atttctgtta   10980
ttacttaaac tacctgatga gttgcgtgca gacatacttt gattctgagt tttccatcac   11040
taacagctcg caccccgatt ctaaccagtc gtggattgaa gacatctctt ttgtgcactc   11100
atatgtcctg acccctgccc agctagggg actgagcaac ctccaatact caaggctcta   11160
cacgaggaac atcggtgacc cgggaactac tgcttttgca gagatcaagc gattagaagc   11220
agtgggtta ctaagtccta gtattatgac taacatctta actaggccgc ctggaaatgg   11280
agattgggcc agtctgtgta acgaccctta ctctttcaat tttgagactg tcgcgagtcc   11340
aaatattgtc cttaagaaac atacacaaag agtcctattt gaaacttgtt caaatccctt   11400
attatctggc gtgcatacag aggataatga ggcagaagag aaggcgttgg ctgaattttt   11460
actcaatcaa gaagtaattc atccacgtgt cgcacatgct atcatggaag caagctctat   11520
aggtaggagg aagcagattc aagggcttgt tgacacaaca aacaccgtaa tcaagattgc   11580
attgactagg aggccacttg gcatcaagag gctgatgcgg atagttaact actcgagcat   11640
gcatgcaatg ctgtttagag acgatgtttt ctcatctaac aggtctaacc accccttagt   11700
ttcctctaat atgtgttctc tgacgctagc agactatgca cggaatagaa gctggtcacc   11760
attgacgggg ggtagaaaga tactgggtgt atctaatcct gatactatag aacttgtaga   11820
gggtgagatc cttagcgtca gcggaggatg cacaagatgt gacagcggag atgaacaatt   11880
cacttggttc catcttccga gcaatataga actgaccgat gacaccagca gaatcctcc   11940
gatgagagtg ccgtacctcg ggtcaaagac tcaagagagg agggccgcct cgcttgcgaa   12000
aatagctcat atgtcaccac atgtgaaagc tgctctaagg gcatcatccg tgttgatctg   12060
ggcttatgga gacaacgaag taaattggac tgctgctctt aaaattgcaa gatctcggtg   12120
caatataaac tcagagtatc ttcgactatt gtcccccctta cccacagctg gaatctcca   12180
acatagactg gatgacggca taactcagat gacattcacc cctgcatctc tctacagggt   12240
gtcaccttat attcacatat ccaatgattc tcaaaggtta ttcacggaag aaggagtcaa   12300
agagggaaat gtagtttatc agcaaatcat gctcttgggt ttatctctaa tcgaatcact   12360
cttcccgatg acgacaacca ggacatacga tgagatcaca ttgcacctcc acagtaaatt   12420
tagctgctgt atcagggaag caccggttgc agttcctttc gagttactcg ggatggcacc   12480
agaactaagg acagtgacct caaataagtt tatgtatgat cctagtcctg tatcggaggg   12540
tgactttgcg agacttgact tagctatctt taagagttat gagcttaatc tagaatcata   12600
tcccacaata gagctaatga acattctttc aatatccagc gggaagttaa tcggccagtc   12660
tgtggttct tatgatgaag atacctccat aaagaatgac gccataatag tgtatgacaa   12720
cacccggaat tggatcagcg aagctcagaa ttcagatgtg gtccgcctat tcgagtatgc   12780
agcacttgaa gtgcttctcg actgttctta tcagctctac tatctgagag taagaggcct   12840
agacaatatc gtgttgtata tgagtgactt atataagaat atgccaggaa ttctacttc   12900
caacattgca gctacaatat ctcatcccat cattcattca agattgcatg cagtaggcct   12960
ggtcaatcac gacgggtcac accaacttgc agacacagat ttcatcgaaa tgtctgcaaa   13020
actattagtc tcttgcactc gacgcgtggt ctcaggttta tatgcaggga ataagtatga   13080
tctgctgttc ccgtctgtct tagatgataa cctgagtgag aagatgcttc agctgatatc   13140
tcggttatgc tgcctgtata cggtgctctt tgctacaaca agagagatcc cgaaaataag   13200
aggcttatct gcagaagaga agtgttcagt acttactgag tacctactgt cagatgctgt   13260
gaaaccatta cttagttctg agcaagtgag ctctatcatg tctcctaaca tagttacgtt   13320
```

```
cccagctaat ctatattaca tgtctcggaa gagccttaat ttgattaggg aaagagagga    13380
cagggacact atcttggcat tgttgttccc ccaagagcca ctacttgagt tccccttagt    13440
acaagatatt ggcgctcgag tgaaagatcc attcacccga caacctgcgg cgttttttaca   13500 agaattagat ttgagcgctc cagcaaggta tgacgcattt acacttagtc aggttcattc    13560
tgaacacaca tcaccaaatc cggaggacga ctacttagta cgatacctgt tcagaggaat    13620
agggaccgcg tcctcctctt ggtataaggc atctcacctt ctttctgtac ctgaggtcag    13680
atgtgcaagg cacgggaatt ccttatactt ggcagaagga agcggagcca ttatgagtct    13740
tctcgaactg catgtgccgc atgagactat ctattacaat acgctcttct caaacgagat    13800 gaaccccca cagcggcatt tcggaccgac cccaacacag tttctgaatt cagttgttta     13860
taggaatcta caggcggagg taccatgtaa ggatggattt gtccaggagt tccgtccatt    13920
atggagagag aatacagaag aaagcgatct gacctcagat aaagcagtgg gttacatcac    13980
atctgcagtg ccctaccggt ctgtatcatt gctgcactgt gacattgaga ttcctccagg    14040
atccaatcaa agcttactgg atcaactggc taccaatctg tctctgattg ccatgcattc    14100
tgtaagggag ggcggggtcg tgatcatcaa agtgttgtat gcaatgggat attacttcca    14160
tctactcatg aacttgttca ctccgtgttc tacgaaagga tatattctct ctaatggcta    14220
tgcatgtaga ggggatatgg agtgttacct ggtatttgtc atgggctatc gagtgggcc     14280 tacatttgta catgaggtag tgaggatggc aaaaactcta gtgcagcggc acggtacact    14340
tttgtccaaa tcagatgaga tcacactgac taggttattt acctcacagc ggcagcgtgt    14400
aacagacatc ctatccagtc ctttaccgag actaataaag ttcttgagaa agaatatcga    14460
tactgcgcta attgaagccg ggggacaacc cgtccgtcca ttctgtgcag agagcttggt    14520
gaggacacta gcggacacaa ctcagatgac ccagatcatc gctagtcaca ttgacacagt    14580
cattcgatct gtgatctaca tggaggctga gggtgatctc gccgacacag tgttcttatt    14640
taccccctac aatctctcta cagacggtaa aaagagaaca tcacttaaac agtgcacaag    14700
gcagatctta gaggtcacaa tattgggtct tagagttgaa aatctcaata agtaggtga     14760 tgtagtcagt ctagtactta aaggtatgat ttctctggag gacctgatcc ctctaagaac    14820
atacttgaag cgtagtacct gccctaagta tttgaagtct gttctaggta ttactaaact    14880
caaagaaatg tttacagaca cctctttatt atacttgact cgtgctcaac aaaaattcta    14940
catgaaaact ataggcaacg cagtcaaggg atactacagt aactgtgact cttaaagata    15000
atcacatatt aataggctcc ttttctagtt aactgagccc ttgttgattt aatgatacta    15060
tattagaaaa aagttgcact ccgatccttt aggactcgtg ttcgaattca ataattgtc     15120 ttagaaaaaa gttgcgcgta attgttcttg aatgtagtcc tgtcattcac caaatctttg    15180
tttggtcggc atggcatctc cacctcctcg cggtccgacc tgggcatccg aaggaggacg    15240
cacgtccact cggatggcta agggagtagc ataaccccttg gggcctcta aacgggtctt    15300 gaggggtttt ttgggcgcgc cgtcgaccga tgcccttgag agccttcaac ccagtcagct    15360
ccttccggtg ggcgcggggc atgactatcg tcgccgcact tatgactgtc ttctttatca    15420
tgcaactcgt aggacaggtg ccggcagcgc tctgggtcat tttcggcgag accgctttc     15480 gctggagcgc gacgatgatc ggcctgtcgc ttgcggtatt cggaatcttg cacgccctcg    15540
ctcaagcctt cgtcactggt cccgccacca aacgtttcgg cgagaagcag gccattatcg    15600
ccggcatggc ggccgacgcg ctgggctacg tcttgctggc gttcgcgacg cgaggctgga    15660
```

```
tggccttccc cattatgatt cttctcgctt ccggcggcat cgggatgccc gcgttgcagg    15720
ccatgctgtc caggcaggta gatgacgacc atcagggaca gcttcaagga tcgctcgcgg    15780
ctcttaccag cctaacttcg atcactggac cgctgatcgt cacggcgatt tatgccgcct    15840
cggcgagcac atgaacgggt ttggcatgga ttgtaggcgc cgccctatac cttgtctgcc    15900
tccccgcgtt gcgtcgcggt gcatggagcc gggccacctc gacctgaatg gaagccggcg    15960
gcacctcgct aacggattca ccactccaag aattggagcc aatcaattct tgcgagaac    16020 tgtgaatgcg caaaccaacc cttggcagaa catatccatc gcgtccgcca tctccagcag    16080
ccgcacgcgg cgcatctcgg gcagcgttgg gtcctggcca cgggtgcgca tgatcgtgct    16140
cctgtcgttg aggacccggc taggctggcg gggttgcctt actggttagc agaatgaatc    16200
accgatacgc gagcgaacgt gaagcgactg ctgctgcaaa acgtctgcga cctgagcaac    16260
aacatgaatg gtcttcggtt tccgtgtttc gtaaagtctg gaaacgcgga agtcagcgcc    16320
ctgcaccatt atgttccgga tctgcatcgc aggatgctgc tggctaccct gtggaacacc    16380
tacatctgta ttaacgaagc gctggcattg accctgagtg attttttctct ggtcccgccg    16440 catccatacc gccagttgtt taccctcaca acgttccagt aaccgggcat gttcatcatc    16500
agtaacccgt atcgtgagca tcctctctcg tttcatcggt atcattaccc ccatgaacag    16560
aaatccccct tacacggagg catcagtgac caaacaggaa aaaccgccc ttaacatggc    16620 ccgctttatc agaagccaga cattaacgct tctggagaaa ctcaacgagc tggacgcgga    16680
tgaacaggca gacatctgtg aatcgcttca cgaccacgct gatgagcttt accgcagctg    16740
cctcgcgcgt ttcggtgatg acggtgaaaa cctctgacac atgcagctcc cggagacggt    16800
cacagcttgt ctgtaagcgg atgccgggag cagacaagcc cgtcagggcg cgtcagcggg    16860
tgttggcggg tgtcggggcg cagccatgac ccagtcacgt agcgatagcg gagtgtatac    16920
tggcttaact atgcggcatc agagcagatt gtactgagag tgcaccatat gcggtgtgaa    16980
ataccgcaca gatgcgtaag gagaaaatac cgcatcaggc gctcttccgc ttcctcgctc    17040
actgactcgc tgcgctcggt cgttcggctg cggcgagcgg tatcagctca ctcaaaggcg    17100
gtaatacggt tatccacaga atcagggggat aacgcaggaa agaacatgtg agcaaaaggc    17160
cagcaaaagg ccaggaaccg taaaaaggcc gcgttgctgg cgtttttcca taggctccgc    17220
ccccctgacg agcatcacaa aaatcgacgc tcaagtcaga ggtggcgaaa cccgacagga    17280
ctataaagat accaggcgtt tccccctgga agctccctcg tgcgctctcc tgttccgacc    17340
ctgccgctta ccggatacct gtccgccttt ctcccttcgg gaagcgtggc gctttctcat    17400
agctcacgct gtaggtatct cagttcggtg taggtcgttc gctccaagct gggctgtgtg    17460
cacgaacccc ccgttcagcc cgaccgctgc gccttatccg gtaactatcg tcttgagtcc    17520
aacccggtaa gacacgactt atcgccactg gcagcagcca ctggtaacag gattagcaga    17580
gcgaggtatg taggcggtgc tacagagttc ttgaagtggt ggcctaacta cggctacact    17640
agaaggacag tatttggtat ctgcgctctg ctgaagccag ttaccttcgg aaaaagagtt    17700
ggtagctctt gatccggcaa acaaaccacc gctggtagcg gtggtttttt tgtttgcaag    17760
cagcagatta cgcgcagaaa aaaaggatct caagaagatc ctttgatctt ttctacgggg    17820
tctgacgctc agtggaacga aaactcacgt taagggattt tggtcatgag attatcaaaa    17880
aggatcttca cctagatcct tttaaattaa aaatgaagtt ttaaatcaat ctaaagtata    17940
tatgagtaaa cttggtctga cagttaccaa tgcttaatca gtgaggcacc tatctcagcg    18000
atctgtctat ttcgttcatc catagttgcc tgactccccg tcgtgtagat aactacgata    18060
```

```
cgggagggct taccatctgg ccccagtgct gcaatgatac cgcgagaccc acgctcaccg   18120
gctccagatt tatcagcaat aaaccagcca gccggaaggg ccgagcgcag aagtggtcct   18180
gcaactttat ccgcctccat ccagtctatt aattgttgcc gggaagctag agtaagtagt   18240
tcgccagtta atagtttgcg caacgttgtt gccattgctg caggcatcgt ggtgtcacgc   18300
tcgtcgtttg gtatggcttc attcagctcc ggttcccaac gatcaaggcg agttacatga   18360
tcccccatgt tgtgcaaaaa agcggttagc tccttcggtc ctccgatcgt tgtcagaagt   18420
aagttggccg cagtgttatc actcatggtt atggcagcac tgcataattc tcttactgtc   18480
atgccatccg taagatgctt ttctgtgact ggtgagtact caaccaagtc attctgagaa   18540
tagtgtatgc ggcgaccgag ttgctcttgc ccggcgtcaa cacgggataa taccgcgcca   18600
catagcagaa ctttaaaagt gctcatcatt ggaaaacgtt cttcggggcg aaaactctca   18660
aggatcttac cgctgttgag atccagttcg atgtaaccca ctcgtgcacc caactgatct   18720
tcagcatctt ttactttcac cagcgtttct gggtgagcaa aaacaggaag gcaaaatgcc   18780
gcaaaaaagg gaataagggc gacacggaaa tgttgaatac tcatactctt ccttttcaa    18840 tattattgaa gcatttatca gggttattgt ctcatgagcg gatacatatt tgaatgtatt   18900
tagaaaaata aacaaatagg ggttccgcgc acatttcccc gaaaagtgcc acctgacgtc   18960
taagaaacca ttattatcat gacattaacc tataaaaata ggcgtatcac gaggcccttt   19020
cgtcttcaag aattctaata cgactcacta tagg                               19054

<210> SEQ ID NO 2
<211> LENGTH: 449
<212> TYPE: PRT
<213> ORGANISM: Artificial Sequence
<220> FEATURE:
<223> OTHER INFORMATION: H domain of M2-LVP-K1

<400> SEQUENCE: 2

Cys Gly Ala Pro Val His Asp Pro Asp Tyr Ile Gly Gly Ile Gly Lys
1               5                   10                  15

Glu Leu Ile Val Asp Asp Ile Ser Asp Val Thr Ser Phe Tyr Pro Ser
            20                  25                  30

Ala Tyr Gln Glu His Leu Asn Phe Ile Pro Ala Pro Thr Thr Gly Ser
        35                  40                  45

Gly Cys Thr Arg Ile Pro Ser Phe Asp Met Ser Thr Thr His Tyr Cys
    50                  55                  60

Tyr Thr His Asn Val Ile Leu Ser Gly Cys Arg Asp His Ser His Ser
65                  70                  75                  80

Tyr Gln Tyr Leu Ala Leu Gly Val Leu Arg Thr Ser Ala Thr Gly Arg
                85                  90                  95

Val Phe Phe Ser Thr Leu Arg Ser Val Asn Leu Asp Asp Thr Gln Asn
            100                 105                 110

Arg Lys Ser Cys Ser Val Ser Ala Thr Pro Leu Gly Cys Asp Met Leu
        115                 120                 125

Cys Ser Lys Val Thr Gly Thr Glu Glu Glu Asp Tyr Lys Ser Val Ala
    130                 135                 140

Pro Thr Ser Met Val His Gly Arg Leu Gly Phe Asp Gly Gln Tyr His
145                 150                 155                 160

Glu Lys Asp Leu Asp Thr Thr Val Leu Phe Lys Asp Trp Val Ala Asn
                165                 170                 175

Tyr Pro Gly Ala Gly Gly Gly Ser Phe Ile Asp Asp Arg Val Trp Phe
```

180                 185                 190
Pro Val Tyr Gly Gly Leu Lys Pro Asn Ser Pro Ser Asp Thr Ala Gln
            195                 200                 205
Glu Gly Lys Tyr Val Ile Tyr Lys Arg His Asn Asn Thr Cys Pro Asp
            210                 215                 220
Glu Gln Asp Tyr Gln Ile Arg Met Ala Lys Ser Ser Tyr Lys Pro Gly
225                 230                 235                 240
Arg Phe Gly Gly Lys Arg Val Gln Gln Ala Ile Leu Ser Ile Lys Val
            245                 250                 255
Ser Thr Ser Leu Gly Lys Asp Pro Val Leu Thr Ile Pro Pro Asn Thr
            260                 265                 270
Ile Thr Leu Met Gly Ala Glu Gly Arg Ile Leu Thr Val Gly Thr Ser
            275                 280                 285
His Phe Leu Tyr Gln Arg Gly Ser Ser Tyr Phe Ser Pro Ala Leu Leu
            290                 295                 300
Tyr Pro Met Thr Val Asn Asn Lys Thr Ala Thr Leu His Ser Pro Tyr
305                 310                 315                 320
Thr Phe Asn Ala Phe Thr Arg Pro Gly Ser Val Pro Cys Gln Ala Ser
            325                 330                 335
Ala Arg Cys Pro Asn Ser Cys Ile Thr Gly Val Tyr Thr Asp Pro Tyr
            340                 345                 350
Pro Leu Ile Phe His Arg Asn His Thr Leu Arg Gly Val Phe Gly Thr
            355                 360                 365
Met Leu Asp Asp Glu Gln Ala Arg Leu Asn Pro Val Ser Ala Val Phe
            370                 375                 380
Asp Asn Ile Ser Arg Ser Arg Val Thr Arg Val Ser Gly Ser Ser Thr
385                 390                 395                 400
Lys Ala Ala Tyr Thr Thr Ser Thr Cys Phe Lys Val Val Glu Thr Asn
            405                 410                 415
Lys Ala Tyr Cys Leu Ser Ile Ala Glu Ile Ser Asn Thr Leu Phe Gly
            420                 425                 430
Glu Phe Arg Ile Val Pro Leu Leu Val Glu Ile Leu Lys Asp Asp Arg
            435                 440                 445
Val

<210> SEQ ID NO 3
<211> LENGTH: 1347
<212> TYPE: DNA
<213> ORGANISM: Artificial Sequence
<220> FEATURE:
<223> OTHER INFORMATION: Mutant H domain plate No.7 C3

<400> SEQUENCE: 3
tgtggagcac ccattcatga tccagattat attggaggaa taggtaaaga acttattgta      60
gatgatgcta gcgacgtcac atcatactat ccctctgcgt tccaagaaca cctgaacttt     120
atcccggcgc tactacagg atcaggttgc actcggatac cctcatttga catgagcgct      180
acccactact gttatactca caatgtgata ttatctggct gcagagatca ctcgcactca     240
catcaatatt tagcacttgg tgtgcttcgg acatctgcaa cagggagggt attcttttcc     300
actctgcgtt ccatcaatct ggatgacacc caaaatcgga agtcttgcag tgtgagtgca     360 accccctttgg gttgtgatat gctgtgctct aaagtcacag agactgaaga agaggattat     420
aactcagcta tccccacgtc gatggtacat ggaaggttag ggttcgacgg ccaataccac     480
gagaaggacc tagatgtcac aacactattc gaggactggg tggcaaacta cccaggagta     540

```
gggggcgggt cttttattga caaccgcgta tggttcccag tttacggagg gctaaaaccc      600
aattcgccca gtgacaccgc acaagaaggg aaatatgtaa tatacaagcg atacaatgac      660
acatgtccag atgagcaaga ttatcagatt caaatggcta agtcttcata taagcctggg      720
cggtttggag ggaaacgcgt acagcaggcc atcttatcta tcaaagtgtc aacatccttg      780
ggcgaggacc cggtactgac tgtaccgccc aacacagtaa cactcatggg ggccgaaggc      840
agagttctca cagtagggac atctcatttc ctttatcagc gagggtcatc atacttctcc      900
cctgccctac tatatcctat gatagtcagc aacaaaacag ccactcttca tagtccttat      960
acattcaatg ccttcactcg accaggtagt gtcccttgcc aggcttcagc aagatgccct     1020
aactcatgtg ttaccggagt ctatactgat ccatatccct tggtcttcta taggaaccac     1080
accttgcgag gggtattcgg gacgatgctt gatgataaac aagcaagact caaccctgta     1140
tctgcagtat ttgacagcat atcccgcagt cgcataaccc gggtgagtgg aagcagcacc     1200
aaggcagcat acacaacatc aacatgtttt aaagttgtaa agaccaataa aacctattgt     1260
ctcagcattg ccgaaatatc caataccctc ttcggggaat tcagaatcgt ccctttacta     1320
gttgagattc tcaaggatga tggggtt                                         1347

<210> SEQ ID NO 4
<211> LENGTH: 1347
<212> TYPE: DNA
<213> ORGANISM: Artificial Sequence
<220> FEATURE:
<223> OTHER INFORMATION: Mutant H domain plate No.13 A6

<400> SEQUENCE: 4
tgtggagcac ccattcatga tccagattat attggaggaa taggtaaaga acttattgta       60
gatgatgcta gcgacgtcac atcatactat ccctctgcgt tccaagaaca cctgaacttt      120
atcccggcgc ctactacagg atcaggttgc actcggatac cctcatttga catgagcgct      180
acccactact gttatactca caatgtgata ttatctggct gcagagatca ctcgcactca      240
catcaatatt tagcacttgg tgtgcttcgg acatctgcaa cagggagggt attcttttcc      300
actctgcgtt ccatcaatct ggatgacacc caaaatcgga agtcttgcag tgtgagtgca      360
acccccttgg gttgtgatat gctgtgctct aaagtcacag agactgaaga agaggattat      420
aactcagcta tcggcacgtc gatggtacat ggaaggttag ggttcgacgg ccaataccac      480
gagaaggacc tagatgtcac aacactattc gaggactggg tggcaaacta cccaggagta      540
gggggcgggt cttttattga caaccgcgta tggttcccag tttacggagg gctaaaaccc      600
aattcgccca gtgacaccgc acaagaaggg aaatatgtaa tatacaagcg atacaatgac      660
acatgtccag atgagcaaga ttatcagatt caaatggcta agtcttcata taagcctggg      720
cggtttggag ggaaacgcgt acagcaggcc atcttatcta tcaaagtgtc aacatccttg      780
ggcgaggacc cggtactgac tgtaccgccc aacacagtaa cactcatggg ggccgaaggc      840
agagttctca cagtagggac atctcatttc ctttatcagc gagggtcatc atacttctcc      900
cctgccctac tatatcctat gatagtcagc aacaaaacag ccactcttca tagtccttat      960
acattcaatg ccttcactcg accaggtagt gtcccttgcc aggcttcagc aagatgccct     1020
aactcatgtg ttaccggagt ctatactgat ccatatccct tggtcttcta taggaaccac     1080
accttgcgag gagtattcgg gacgatgctt gatgataaac aagcaagact caaccctgta     1140
tctgcagtat ttgacagcat atcccgcagt cgcataaccc gggtgagttc aagcagcacc     1200
```

| | |
|---|---|
| aaggcagcat acacaacatc aacatgtttt aaagttgtaa agaccaataa aacctattgt | 1260 |
| ctcagcattg ccgaaatatc caatacccte ttcggggaat tcagaatcgt cccttttacta | 1320 |
| gttgagattc tcaaggatga tggggtt | 1347 |

<210> SEQ ID NO 5
<211> LENGTH: 1347
<212> TYPE: DNA
<213> ORGANISM: Artificial Sequence
<220> FEATURE:
<223> OTHER INFORMATION: Muntant H domain plate No.22 H9

<400> SEQUENCE: 5

| | |
|---|---|
| tgtggagcac ccattcatga tccagattat attggaggaa taggtaaaga acttattgta | 60 |
| gatgatgcta gcgacgtcac atcatactat ccctctgcgt tccaagaaca cctgaacttt | 120 |
| atcccggcgc ctactacagg atcaggttgc actcggatac cctcatttga catgagcgat | 180 |
| acccactact gttatactca caatgtgata ttatctggct gcagagatca ctcgcactca | 240 |
| catcaatatt tagcacttgg tgtgcttcgg acatctgcaa cagggagggt attcttttcc | 300 |
| actctgcgtt ccatcaatct ggatgacacc caaaatcgga agtcttgcag tgtgagtgca | 360 |
| accccttgg gttgtgatat gctgtgctct aaagtcacag agactgaaga agaggattat | 420 |
| aactcagcta tccccacgtc gatggtacat ggaaggttag ggttcgacgg ccaataccac | 480 |
| gagaaggacc tagatgtcac aacactattc gaggactggg tggcaaacta cccaggagta | 540 |
| gggggcgggt cttttattga caaccgcgta tggttcccag tttacggagg gctaaaaccc | 600 |
| aattcgccca gtgacaccgc acaagaaggg aaatatgtaa tatacaagcg atacaatgac | 660 |
| acatgtccag atgagcaaga ttatcagatt caaatggcta agtcttcata taagcctggg | 720 |
| cggtttggag ggaaacgcgt acagcaggcc atcttatcta tcaaagtgtc aacatccttg | 780 |
| ggcgaggacc cggtactgac tgtaccgccc aacacagtaa cactcatggg ggccgaaggc | 840 |
| agagttctca cagtagggac atctcatttc ctttatcagc gagggtcatc atacttctcc | 900 |
| cctgccctac tatatcctat gatagtcagc aacaaaacag ccactcttca tagtccttat | 960 |
| acattcaatg ccttcactcg accaggtagt gtcccttgcc aggcttcagc aagatgccct | 1020 |
| aactcatgtg ttaccggagt ctatactgat ccatatccct tggtcttcta taggaaccac | 1080 |
| accttgcgag gggtattcgg gacgatgctt gatgataaac aagcaagact caaccctgta | 1140 |
| tctgcagtat ttgacagcat atcccgcagt cgcataaccc gggtgagttc aagcagcacc | 1200 |
| aaggcagcat acacaacatc aacatgtttt aaagttgtaa agaccaataa aacctattgt | 1260 |
| ctcagcattg ccgaaatatc caatacccte ttcggggaat tcagaatcgt cccttttacta | 1320 |
| gttgagattc ttaaggatga tggggtt | 1347 |

<210> SEQ ID NO 6
<211> LENGTH: 1347
<212> TYPE: DNA
<213> ORGANISM: Artificial Sequence
<220> FEATURE:
<223> OTHER INFORMATION: Muntant H domain plate No.30 E3

<400> SEQUENCE: 6

| | |
|---|---|
| tgtggagcac ccattcatga tccagattat attggaggaa taggtaaaga acttattgta | 60 |
| gatgatgcta gcgacgtcac atcatactat ccctctgcgt tccaagaaca cctgaacttt | 120 |
| atcccggcgc ctactacagg atcaggttgc actcggatac cctcatttga catgagcgct | 180 |
| acccactact gttatactca caatgtgata ttatctggct gcagagatca ctcgcactca | 240 |

```
catcaatatt tagcacttgg tgtgcttcgg acatctgcaa cagggagggt attcttttcc      300
actctgcgtt ccatcaatct ggatgacacc caaaatcgga agtcttgcag tgtgagtgca      360
accccctggg gttgtgatat gctgtgctct aaagtcacag agactgaaga agaggattat      420
aactcagcta tccccacgtc gatggtacat ggaaggttag ggttcgacgg ccaataccac      480
gagaaggacc tagatgtcac aacactattc gaggactggg tggcaaacta cccaggagta      540
gggggcgggt cttttattga caaccgcgta tggttcccag tttacggagg gctaaaaccc      600
aattcgccca gtgacaccgc acaagaaggg aaatatgtaa tatacaagcg atacaatgac      660
acatgtccag atgagcaaga ttatcagatt caaatggcta agtcttcata taagcctggg      720
cggtttggag ggaaacgcgt acagcaggcc atcttatcta tcaaagtgtc aacatccttg      780
ggcgaggacc cggtactgac tgtaccgccc aacacagtaa cactcatggg ggccgaaggc      840
agagttctca cagtagggac atctcatttc ctttatcagc gagggccatc atacttctcc      900
cctgccctac tatatcctat gatagtcagc aacaaaacag ccactcttca tagtccttat      960
acattcaatg ccttcactcg accaggtagt gtcccttgcc aggcttcagc aagatgccct     1020
aactcatgtg ttaccggagt ctatactgat ccatatccct tggtcttcta taggaaccac     1080
accttgcgag gggtattcgg gacgatgctt gatgataaac aagcaagact caaccctgta     1140
tctgcagtat ttgacagcat atcccgcagt cgcataaccc gggtgagttc aagcagcacc     1200
aaggcagcat acacaacttc aacatgtttt aaagttgtaa agaccaataa aacctattgt     1260
ctcagcattg ccgaaatatc caataccctc ttcggggaat tcagaatcgt ccctttacta     1320
gttgagattc tcaaggatga tggggtt                                         1347
```

<210> SEQ ID NO 7
<211> LENGTH: 1347
<212> TYPE: DNA
<213> ORGANISM: Artificial Sequence
<220> FEATURE:
<223> OTHER INFORMATION: Mutant H domain plate No.47 F8

<400> SEQUENCE: 7

```
tgtggagcac ccattcatga tccagattat attggaggaa taggtaaaga acttattgta       60
gatgatgcta gcgacgtcac atcatactat ccctctgcgt tccaagaaca cctgaacttt      120
atcccggcgc ctactacagg atcaggttgc actcggatac cctcatttga catgagcgct      180
acccactact gttatactca caatgtgata ttatctggct gcagagatca ctcgcactca      240
catcaatatt tagcacttgg tgtgcttcgg acatctgcaa cagggagggt attcttttcc      300
actctgcgtt ccatcaatct ggatgacacc caaaatcgga agtcttgcag tgtgagtgca      360
accccctggg gttgtgatat gctgtgctct aaagtcacag agactgaaga agaggattat      420
aactcagcta tccccacgtc gatggtacat ggaaggttag ggttcgacgg ccaataccac      480
gagaaggacc tagatgtcac aacactattc gaggactggg tggcaaacta cccaggagta      540
gggggcgggt cttttattga caaccgcgta tggttcccag tttacggagc gctaaaaccc      600
aattcgcgca gtgacaccgc acaagaaggg aaatatgtaa tatacaagcg atacaatgac      660
acatgtccag atgagcaaga ttatcagatt caaatggcta agtcttcata taagcctggg      720
cggtttggag ggaaacgcgt acagcaggcc atcttatcta tcaaagtgtc aacatccttg      780
ggcgaggacc cggtactgac tgtaccgcac aacacagtaa cactcatggg ggccgaaggc      840
agagttctca cagtagggac atctcatttc ctttatcagc gagggtcatc atacttctcc      900
```

| | |
|---|---|
| cctgccctac tatatcctat gatagtcagc aacaaaacag ccactcttca tagtccttat | 960 |
| acattcaatg ccttcactcg accaggtagt gtcccttgcc aggcttcagc aagatgccct | 1020 |
| aactcatgtg ttaccggagt ctatactgat ccatatccct tggtcttcta taggaaccac | 1080 |
| accttgcgag gggtattcgg gacgatgctt gatgataaac aagcaagact caaccctgta | 1140 |
| tctgcagtat ttgacagcat atcccgcagt cgcataaccc gggtgagttc aagcagcacc | 1200 |
| aaggcagcat acacaacatc aacatgtttt aaagttgtaa agaccaataa aacctattgt | 1260 |
| ctcagcattg ccgaaatatc caataccctc ttcggggaat tcagaatcgt ccctttacta | 1320 |
| gttgagattc tcaaggatga tggggtt | 1347 |

<210> SEQ ID NO 8
<211> LENGTH: 1347
<212> TYPE: DNA
<213> ORGANISM: Newcastle disease virus
<220> FEATURE:
<221> NAME/KEY: gene
<222> LOCATION: (1)..(1347)
<223> OTHER INFORMATION: H domain of hemagglutinin-neuraminidase

<400> SEQUENCE: 8

| | |
|---|---|
| tgtggagcac ccattcatga tccagattat attggaggaa taggtaaaga acttattgta | 60 |
| gatgatgcta gcgacgtcac atcatactat ccctctgcgt tccaagaaca cctgaacttt | 120 |
| atcccggcgc ctactacagg atcaggttgc actcggatac cctcatttga catgagcgct | 180 |
| acccactact gttatactca caatgtgata ttatctggct gcagagatca ctcgcactca | 240 |
| catcaatatt tagcacttgg tgtgcttcgg acatctgcaa cagggagggt attcttttcc | 300 |
| actctgcgtt ccatcaatct ggatgacacc caaaatcgga agtcttgcag tgtgagtgca | 360 |
| accccttgg gttgtgatat gctgtgctct aaagtcacag agactgaaga agaggattat | 420 |
| aactcagcta tccccacgtc gatggtacat ggaaggttag ggttcgacgg ccaataccac | 480 |
| gagaaggacc tagatgtcac aacactattc gaggactggg tggcaaacta cccaggagta | 540 |
| gggggcgggt cttttattga caaccgcgta tggttcccag tttacggagg ctaaaaccc | 600 |
| aattcgccca gtgacaccgc acaagaaggg aaatatgtaa tatacaagcg atacaatgac | 660 |
| acatgtccag atgagcaaga ttatcagatt caaatggcta agtcttcata taagcctggg | 720 |
| cggtttggag ggaaacgcgt acagcaggcc atcttatcta tcaaagtgtc aacatccttg | 780 |
| ggcgaggacc cggtactgac tgtaccgccc aacacagtaa cactcatggg ggccgaaggc | 840 |
| agagttctca cagtagggac atctcatttc ctttatcagc gagggtcatc atacttctcc | 900 |
| cctgccctac tatatcctat gatagtcagc aacaaaacag ccactcttca tagtccttat | 960 |
| acattcaatg ccttcactcg accaggtagt gtcccttgcc aggcttcagc aagatgccct | 1020 |
| aactcatgtg ttaccggagt ctatactgat ccatatccct tggtcttcta taggaaccac | 1080 |
| accttgcgag gggtattcgg gacgatgctt gatgataaac aagcaagact caaccctgta | 1140 |
| tctgcagtat ttgacagcat atcccgcagt cgcataaccc gggtgagttc aagcagcacc | 1200 |
| aaggcagcat acacaacatc aacatgtttt aaagttgtaa agaccaataa aacctattgt | 1260 |
| ctcagcattg ccgaaatatc caataccctc ttcggggaat tcagaatcgt ccctttacta | 1320 |
| gttgagattc tcaaggatga tggggtt | 1347 |

<210> SEQ ID NO 9
<211> LENGTH: 30
<212> TYPE: DNA
<213> ORGANISM: Artificial Sequence

```
<220> FEATURE:
<223> OTHER INFORMATION: L2 primer_F

<400> SEQUENCE: 9
acgcgtggtc tcaggtttat atgcagggaa                                           30

<210> SEQ ID NO 10
<211> LENGTH: 31
<212> TYPE: DNA
<213> ORGANISM: Artificial Sequence
<220> FEATURE:
<223> OTHER INFORMATION: L2 primer_R

<400> SEQUENCE: 10
ttaattaaac caaacaaaga tttggtgaat g                                         31

<210> SEQ ID NO 11
<211> LENGTH: 30
<212> TYPE: DNA
<213> ORGANISM: Artificial Sequence
<220> FEATURE:
<223> OTHER INFORMATION: L1 primer_F

<400> SEQUENCE: 11
actagttgag attctcaagg atgatggggt                                           30

<210> SEQ ID NO 12
<211> LENGTH: 30
<212> TYPE: DNA
<213> ORGANISM: Artificial Sequence
<220> FEATURE:
<223> OTHER INFORMATION: L1 primer_R

<400> SEQUENCE: 12
acgcgtcgag tgcaagagac taatagtttt                                           30

<210> SEQ ID NO 13
<211> LENGTH: 29
<212> TYPE: DNA
<213> ORGANISM: Artificial Sequence
<220> FEATURE:
<223> OTHER INFORMATION: F-HN primer_F

<400> SEQUENCE: 13
ggcgccatta tcggtggtgt agctctcgg                                            29

<210> SEQ ID NO 14
<211> LENGTH: 30
<212> TYPE: DNA
<213> ORGANISM: Artificial Sequence
<220> FEATURE:
<223> OTHER INFORMATION: F-HN primer_R

<400> SEQUENCE: 14
actagtaaag gacgattct gaattccccg                                            30

<210> SEQ ID NO 15
<211> LENGTH: 30
<212> TYPE: DNA
<213> ORGANISM: Artificial Sequence
<220> FEATURE:
<223> OTHER INFORMATION: P-M-F primer_F

<400> SEQUENCE: 15
ccgcggaaac agccaagaga gaccgcagaa                                           30
```

<210> SEQ ID NO 16
<211> LENGTH: 33
<212> TYPE: DNA
<213> ORGANISM: Artificial Sequence
<220> FEATURE:
<223> OTHER INFORMATION: P-M-F primer_R

<400> SEQUENCE: 16
ggcgccaacc gggatccaga atcttctacc cgt                                    33

<210> SEQ ID NO 17
<211> LENGTH: 30
<212> TYPE: DNA
<213> ORGANISM: Artificial Sequence
<220> FEATURE:
<223> OTHER INFORMATION: NP-P primer_F

<400> SEQUENCE: 17
gtttaaacac caaacagaga atccgtaagg                                        30

<210> SEQ ID NO 18
<211> LENGTH: 30
<212> TYPE: DNA
<213> ORGANISM: Artificial Sequence
<220> FEATURE:
<223> OTHER INFORMATION: NP-P primer_R

<400> SEQUENCE: 18
ccgcggcttt gttgactccc ctgttgttga                                        30

<210> SEQ ID NO 19
<211> LENGTH: 19
<212> TYPE: DNA
<213> ORGANISM: Artificial Sequence
<220> FEATURE:
<223> OTHER INFORMATION: HN opti EP primer_F

<400> SEQUENCE: 19
tgtggtgcgc caattcatg                                                    19

<210> SEQ ID NO 20
<211> LENGTH: 21
<212> TYPE: DNA
<213> ORGANISM: Artificial Sequence
<220> FEATURE:
<223> OTHER INFORMATION: HN opti avidin primer_R

<400> SEQUENCE: 20
ttactccttc tgggtgcgca g                                                 21

<210> SEQ ID NO 21
<211> LENGTH: 22
<212> TYPE: DNA
<213> ORGANISM: Artificial Sequence
<220> FEATURE:
<223> OTHER INFORMATION: Mutation H domain primer_F

<400> SEQUENCE: 21
ggtgagtgga agcagcacca ag                                                22

<210> SEQ ID NO 22
<211> LENGTH: 19
<212> TYPE: DNA
<213> ORGANISM: Artificial Sequence
<220> FEATURE:
<223> OTHER INFORMATION: Mutation H domain primer_R

```
<400> SEQUENCE: 22
cgggttatgc gactgcggg                                                19

<210> SEQ ID NO 23
<211> LENGTH: 23
<212> TYPE: DNA
<213> ORGANISM: Artificial Sequence
<220> FEATURE:
<223> OTHER INFORMATION: NDV check primer_F

<400> SEQUENCE: 23
ccacaattcc aagataaccg gag                                           23

<210> SEQ ID NO 24
<211> LENGTH: 23
<212> TYPE: DNA
<213> ORGANISM: Artificial Sequence
<220> FEATURE:
<223> OTHER INFORMATION: NDV check primer_R

<400> SEQUENCE: 24
gctgccacaa tcagatgcct ttg                                           23

<210> SEQ ID NO 25
<211> LENGTH: 25
<212> TYPE: DNA
<213> ORGANISM: Artificial Sequence
<220> FEATURE:
<223> OTHER INFORMATION: Vaccinia virus check primer_F

<400> SEQUENCE: 25
atgacgatga aaatgatggt acata                                         25

<210> SEQ ID NO 26
<211> LENGTH: 25
<212> TYPE: DNA
<213> ORGANISM: Artificial Sequence
<220> FEATURE:
<223> OTHER INFORMATION: Vaccinia virus check primer_R

<400> SEQUENCE: 26
ctccaatact actgtagttg taagg                                         25
```